(12) United States Patent
Bar-Shir et al.

(10) Patent No.: US 10,753,892 B2
(45) Date of Patent: Aug. 25, 2020

(54) NON-INVASIVE SENSING OF FREE METAL IONS USING ION CHEMICAL EXCHANGE SATURATION TRANSFER

(71) Applicant: The Johns Hopkins University, Baltimore, MD (US)

(72) Inventors: Amnon Bar-Shir, Baltimore, MD (US); Jeff W. M. Bulte, Fulton, MD (US); Michael T. McMahon, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 641 days.

(21) Appl. No.: 14/785,486

(22) PCT Filed: Apr. 18, 2014

(86) PCT No.: PCT/US2014/034671
§ 371 (c)(1),
(2) Date: Oct. 19, 2015

(87) PCT Pub. No.: WO2014/172651
PCT Pub. Date: Oct. 23, 2014

(65) Prior Publication Data
US 2016/0091443 A1    Mar. 31, 2016

Related U.S. Application Data

(60) Provisional application No. 61/813,881, filed on Apr. 19, 2013.

(51) Int. Cl.
*G01N 24/08* (2006.01)
*A61B 5/055* (2006.01)
(Continued)

(52) U.S. Cl.
CPC ............ *G01N 24/08* (2013.01); *A61B 5/055* (2013.01); *A61K 49/10* (2013.01); *C07C 229/40* (2013.01);
(Continued)

(58) Field of Classification Search
None
See application file for complete search history.

(56) References Cited

U.S. PATENT DOCUMENTS

| | | | | |
|---|---|---|---|---|
| 5,516,911 A | * | 5/1996 | London | C07C 205/37 548/236 |
| 2003/0053954 A1 | | 3/2003 | Meade et al. | |

(Continued)

OTHER PUBLICATIONS

Langereis, S. et al. "A Temperature-Sensitive Liposomal 1H CEST and 19F Contrast Agent for MR Image-Guided Drug Delivery," J. Am. Chem. Soc., 2009, 131 (4), pp. 1380-1381 (Year: 2009).*

(Continued)

*Primary Examiner* — Christopher Adam Hixson
*Assistant Examiner* — Michelle Adams
(74) *Attorney, Agent, or Firm* — Mintz Levin Cohn Ferris Glovsky and Popeo, P.C.; Peter F. Corless

(57) ABSTRACT

The invention features a novel non-invasive approach for imaging, detecting and/or sensing metal ions with improved sensitivity and specificity in a biological sample or tissue. In certain embodiments, the invention provides a MR contrast-based approach for imaging, detecting and/or sensing metal ions in the biological sample/tissue containing various background ions by using $^{19}F$-based chemical exchange saturation transfer (CEST) technique.

17 Claims, 20 Drawing Sheets

(51) Int. Cl.
*A61K 49/10* (2006.01)
*G01R 33/485* (2006.01)
*G01R 33/56* (2006.01)
*C07C 229/40* (2006.01)
*G01R 33/46* (2006.01)
*G01R 33/465* (2006.01)
*G01R 33/28* (2006.01)

(52) U.S. Cl.
CPC ....... *G01R 33/485* (2013.01); *G01R 33/5601* (2013.01); *G01R 33/5605* (2013.01); *G01R 33/281* (2013.01); *G01R 33/465* (2013.01); *G01R 33/4608* (2013.01)

(56) References Cited

U.S. PATENT DOCUMENTS

| | | |
|---|---|---|
| 2005/0232866 A1 | 10/2005 | Melchior et al. |
| 2006/0193781 A1 | 8/2006 | Frederickson et al. |
| 2009/0196830 A1 | 8/2009 | Lamerichs et al. |
| 2009/0275829 A1 | 11/2009 | Agarwal et al. |
| 2011/0177009 A1* | 7/2011 | Langereis ............ A61K 49/12 424/9.363 |

OTHER PUBLICATIONS

Gilboa, H. et al. "19F NMR magnetization transfer between 5-FBAPTA and its complexes. An alternative means or measuring free Ca2+ concentration, and detection of complexes with protein in erythrocytes," NMR in Biomedicine, vol. 7, Issue 7 Nov. 1994, pp. 330-338 (Year: 1994).*

Bar-Shir, A. et al. "Metal Ion Sensing Using Ion Chemical Exchange Saturation Transfer 19F Magnetic Resonance Imaging," J. Am. Chem. Soc. 2013, 135, 33, 12164-12167. Publication Date: Aug. 1, 2013 (Year: 2013).*

SciFinder record for CAS Registry Number: 156638-52-7, "Glycine, N,N'-[1,2-ethanediylbis[oxy(3,4-difluoro-2,1-phenylene)]]bis[N-(carboxymethyl)-," downloaded on Mar. 25, 2020. (Year: 2020).*

* cited by examiner

NON-INVASIVE SENSING OF FREE METAL IONS USING ION CHEMICAL EXCHANGE SATURATION TRANSFER

RELATED APPLICATIONS

This application is the U.S. national stage pursuant to 35 U.S.C. § 371, of United States international application Ser. No. PCT/US2014/034671, filed Apr. 18, 2014 and published in English on Oct. 23, 2014 as publication WO2014/172651 A1, which claims the benefit of priority of U.S. Provisional Application No. 61/813,881, filed Apr. 19, 2013, which are hereby expressly incorporated by reference in their entirety.

STATEMENT REGARDING FEDERALLY-SPONSORED RESEARCH

This invention was made with government support under grant numbers EB007825 and EB012590, awarded by the National Institutes of Health. The government has certain rights in the invention.

FIELD OF INVENTION

The present invention generally relates to methods of magnetic resonance imaging (MRI), more particularly MRI that is based on chemical exchange saturation transfer (CEST) and more specifically CEST based MRI that utilizes $^{19}F$-based responsive MRI contrast agents.

BACKGROUND OF THE INVENTION

Metal ions play a crucial role in a myriad of biological processes, and the ability to monitor real time changes in metal ion concentrations is essential for understanding a variety of physiological events. Alterations in cellular homeostasis of metal ions are connected to human disorders and diseases including cancer, diabetes, and neurodegenerative disease (Nat. Chem. Biol., 2008; 4: 168-175). As demonstrated in the cartoon of FIG. 1, metal ion signaling and homeostasis play an important role in many cellular processes. The main metal ions involved are the monovalent sodium and potassium, and the bivalent calcium, zinc magnesium and iron. Cells maintain healthy levels of the essential metal ions using several classes of proteins. Currently, imaging dynamic changes in metal ions levels is restricted to fluorescence-based methodologies which are limited by low tissue penetration and thus do not allow in vivo imaging of metal ions in deep tissues or organs.

Chemical exchange saturation transfer (CEST) MR imaging is a technique in which low-concentration marker molecules are labeled by saturating their exchangeable protons (e.g., hydroxyl, amine, amide, or imino protons) by radiofrequency (RF) irradiation. If such saturation can be achieved rapidly (i.e., before the proton exchanges), exchange of such labeled protons with water leads to progressive water saturation, allowing indirect detection of the solute via the water resonance through a decrease in signal intensity in MRI [Ward, K. M., Aletras, A. H. & Balaban, R. S. A new class of contrast agents for MRI based on proton chemical exchange dependent saturation transfer (CEST). *J Magn Reson* 143, 79-87 (2000)].

Each CEST contrast agent can have a different saturation frequency, which depends on the chemical shift of the exchangeable proton. The magnitude of proton transfer enhancement (PTE) due to this effect, and the resulting signal reduction from equilibrium ($S_0$) to saturated (S), are given by [Goffeney, N., Bulte, J. W., Duyn, J., Bryant, L. H., Jr. & van Zijl, P. C. Sensitive NMR detection of cationic-polymer-based gene delivery systems using saturation transfer via proton exchange. *J Am Chem Soc* 123, 8628-8629 (2001)]:

$$PTE = \frac{NM_w \alpha k_{ex}}{(1-x_{CA})R_{1wat} + x_{CA}k_{ex}} \cdot \{1 - e^{-[(1-x_{CA})R_{1wat} + x_{CA}k_{ex}]t_{sat}}\}, \quad [\text{Eq. 1}]$$

$$\text{and } (1 - S_{sat}/S_0) = \frac{PTE \cdot [CA]}{2 \cdot [H_2O]}. \quad [\text{Eq. 2}]$$

"CA" is the contrast agent containing multiple exchangeable protons, $x_{CA}$ its fractional exchangeable proton concentration, a the saturation efficiency, k the pseudo first-order rate constant, N the number of exchangeable protons per molecular weight unit, and $M_w$ the molecular weight of the CA. The exponential term describes the effect of back exchange and water longitudinal relaxation ($R_{1wat}=1/T_{1wat}$) on the transfer during the RF saturation period ($t_{sat}$). This effect will be bigger when protons exchange faster, but the catch is that saturation occurs faster as well, which increases the radio-frequency power needed. In addition, the resonance of the particular protons must be well separated from water in the proton NMR spectrum, which requires a slow exchange on the NMR time scale. This condition means that the frequency difference of the exchangeable protons with water is much larger than the exchange rate ($\Delta\omega > k$).

Thus, the CEST technology becomes more applicable at higher magnetic fields or when using paramagnetic shift agents [Mang, S., Merritt, M., Woessner, D. E., Lenkinski, R. E. & Sherry, A. D. PARACEST agents: modulating MRI contrast via water proton exchange. *Acc Chem Res* 36, 783-790 (2003)]. Any molecule that exhibits a significant PTE effect can be classified as a CEST (contrast) agent. The concept of these agents as MR contrast agents is somewhat similar to the chemical amplification of colorimetric labels in in situ gene expression assays. CEST agents can be detected by monitoring the water intensity as a function of the saturation frequency, leading to a so-called z-spectrum. In such spectra, the saturation effect of the contrast agent on the water resonance is displayed as a function of irradiation frequency.

Since the first report of CEST contrast in 2000, CEST MR imaging has become widely used MRI contrast mechanism (demonstrated in FIG. 2). FIG. 2 shows that a CEST contrast is generated by the dynamic exchange process between an exchangeable proton of a biomarker of interest and the surrounding water protons. To detect the biomarkers, the magnetization of some of their exchangeable protons is nullified by applying a selective radiofrequency saturation pulse at the specific resonance frequency (chemical shift) of the target protons. Due to exchange of the "saturated" agent protons with surrounding water protons, the net water signal is reduced thus enhancing the MRI contrast.

CEST-MRI has been employed for many applications in molecular and cellular MRI (see, e.g., Bar-Shir, A. et al., *J. Am Chem. Soc.* 2013; Ratnakar, S. J. et al., *J. Am Chem. Soc.* 2012, 134, 5798; Liu, G. et al., Magn Reson Med. 2012, 67, 1106; Longo, D. L. et al., Magn Reson Med. 2012, doi: 10.1002/mrm. 24513; Li., Y. et al. *Contrast Media Mol Imaging* 2011, 6, 219; Aime, S. et al. *Angew Chem Int Ed Engl* 2005, 44, 1813; Chan, K. W. et al., *Nat Mat* 2013, 12, 268; Liu, G. et al., *NMR in Biomedicine* 2013, doi: 10.1002/nbm.2899).

However, despite that recent advances in the field of molecular magnetic resonance imaging (MRI) has led to the development of new strategies in the design and synthesis of responsive MRI contrast agents for detecting biologically relevant metal ions, the specificity and sensitivity of those probes is limited.

Therefore, there is a need for the development of novel methodology and responsive MRI contrast agents for detecting biologically relevant metal ions with improved specificity and sensitivity.

SUMMARY OF THE INVENTION

The present invention features a novel method of detecting biologically relevant metal ions. In particular embodiments, the invention utilizes chemical exchange saturation transfer (CEST) MR technique for imaging a metal ion in a biological sample or tissue.

In one aspect, the invention provides a method of obtaining a magnetic resonance (MR) image of a metal ion in a biological sample or tissue. The method comprises a) introducing a $^{19}$F-based responsive magnetic resonance imaging (MRI) contrast agent to a biological sample or tissue containing the metal ion; and b) imaging the biological sample or tissue using a chemical exchange saturation transfer (CEST)-based MRI technique.

In another aspect, the invention relates to a method of detecting or sensing a metal ion in a biological sample or tissue comprising background ions. Specifically, the method comprises steps of a) introducing to the biological sample or tissue $^{19}$F-based responsive magnetic resonance imaging (MRI) contrast agents, wherein at least one of the $^{19}$F-based responsive MRI contrast agents is bound to the metal ion to produce a chelation complex;

b) radiofrequency (RF) labeling of $^{19}$F frequency in said chelation complex; and c) detecting label transfer to $^{19}$F frequency in a $^{19}$F-based responsive MRI contrast agent free of a metal ion chelation.

In certain embodiments, the method further includes a step of detecting a chemical shift change of $^{19}$F by using a $^{19}$F nuclear magnetic resonance (NMR) technique.

Specifically, provided herein is a method of detecting or sensing $Ca^{2+}$ in a biological sample or tissue comprising background ions. The method comprises steps of a) introducing to the biological sample or tissue a $^{19}$F-derivative of 1,2,-bis(o-aminophenoxy)ethane-N,N,N',N', tetra-acetic acid (BAPTA), or a salt or ester thereof to obtain a chelation complex containing the metal ion and the $^{19}$F-derivative; and b) detecting a chemical shift change of $^{19}$F through a $^{19}$F NMR.

As used herein, the background ions refer to other metal ions or other types of ions that are present in the biological sample or tissue, which are not the interest for imaging/or detecting.

Also featured herein are kits for MRI imaging of free metal ions in a biological sample or tissue. The kit of the invention includes one or more $^{19}$F-based responsive MRI contrast agents of the invention (details provided infra.), and instructions for imaging free metal ions in the biological sample or tissue.

Also featured are MRI methods that embody the use of the responsive MRI contrast agents of the invention.

Other aspects and embodiments of the invention are discussed below.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein.

µT/2000 ms at 37° C.; the Δω dependency between $Ca^{2+}$-bound and free 5F-BAPTA was obtained from $^{19}$F-iCEST Z-spectra.

FIG. 12a-g) show sensing $Ca^{2+}$ using iCEST: a) alignment of four tubes containing 5 mM of 5F-BAPTA (pH=7.2) and different molar fractions (χCa=1:250, 1:500, 1:1000, 1:0) between $Ca^{2+}$ and 5F-BAPTA for the phantom (pH=7.2, 16.4 T, 37° C.); b) 1H-MR image, c) 19F-MR image; and d) overlay of $^{19}$F-iCEST image (Δω=6.2 ppm) on $^{19}$F-image; e) iCEST Z-spectra for a tube with χCa=1:1000; and f) iCEST Z-spectra for a tube with χCa=1:500 Samples; solid lines represent Bloch simulations; g) plot of χCa vs. MTRasym for iCEST data acquired at $B_1$=3.6 $t_{sat}$=1.5 s; a 5% threshold is shown as a gray dashed line, which is reached at χCa=1: 2000.

Figures 13A, 13B, 13C:
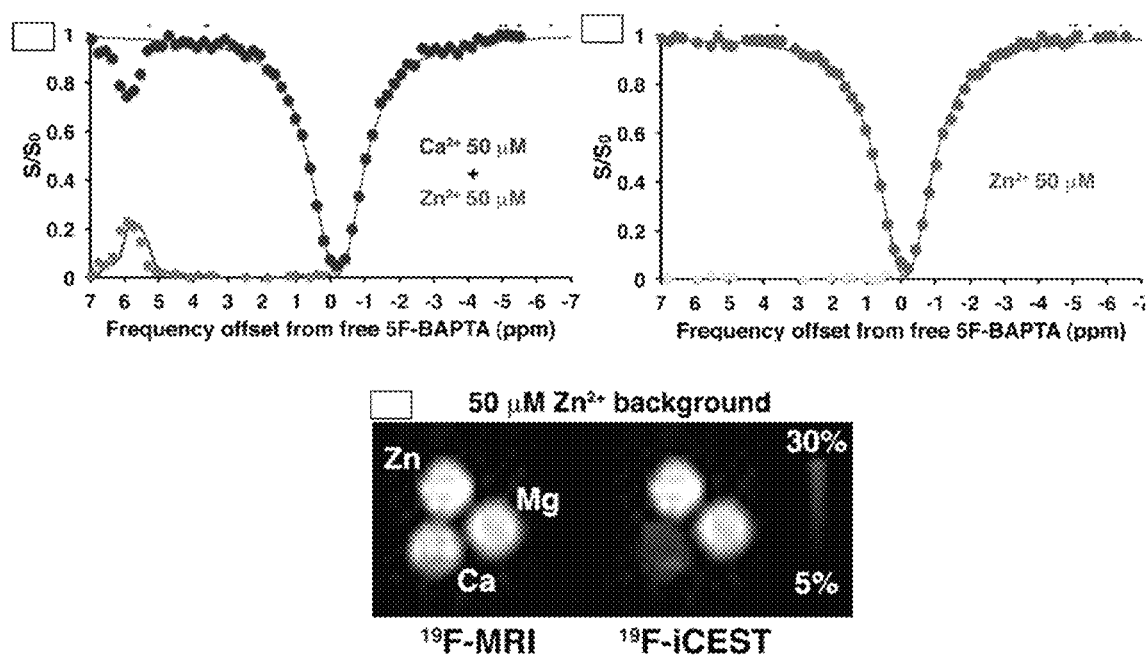

FIGS. 13a-c) demonstrate $Ca^{2+}$ specificity of 5F-BAPTA in a $Zn^{2+}$ background.

Figures 14A, 14B, 14C:
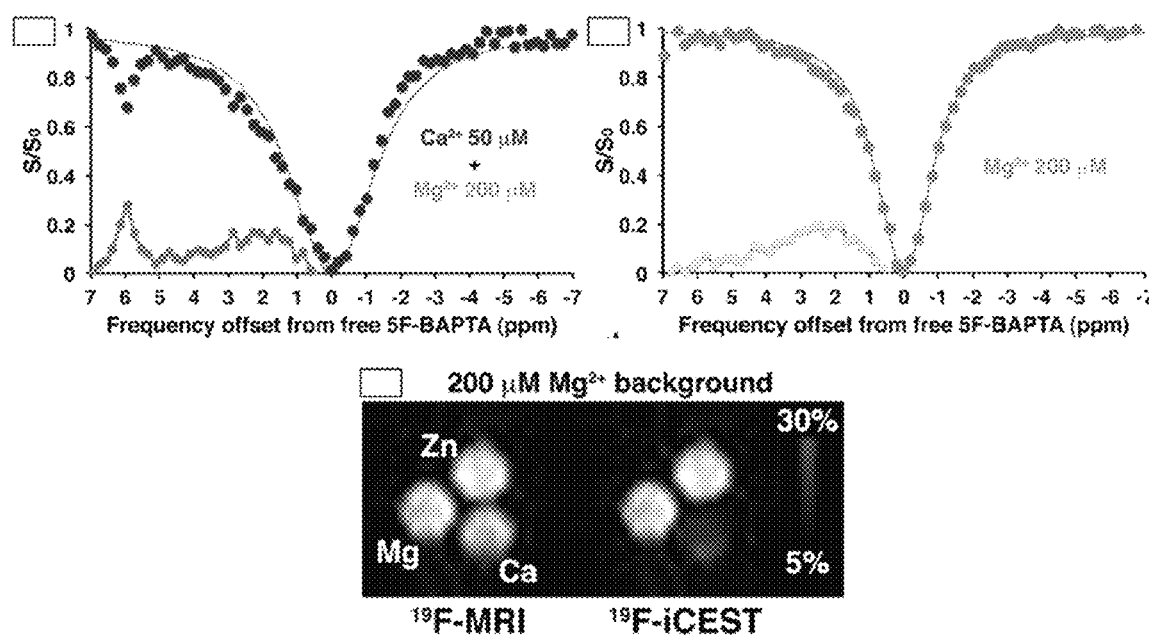

FIGS. 14a-c) demonstrate $Ca^{2+}$ specificity of 5F-BAPTA in a $Mg^{2+}$ background.

Figure 15:
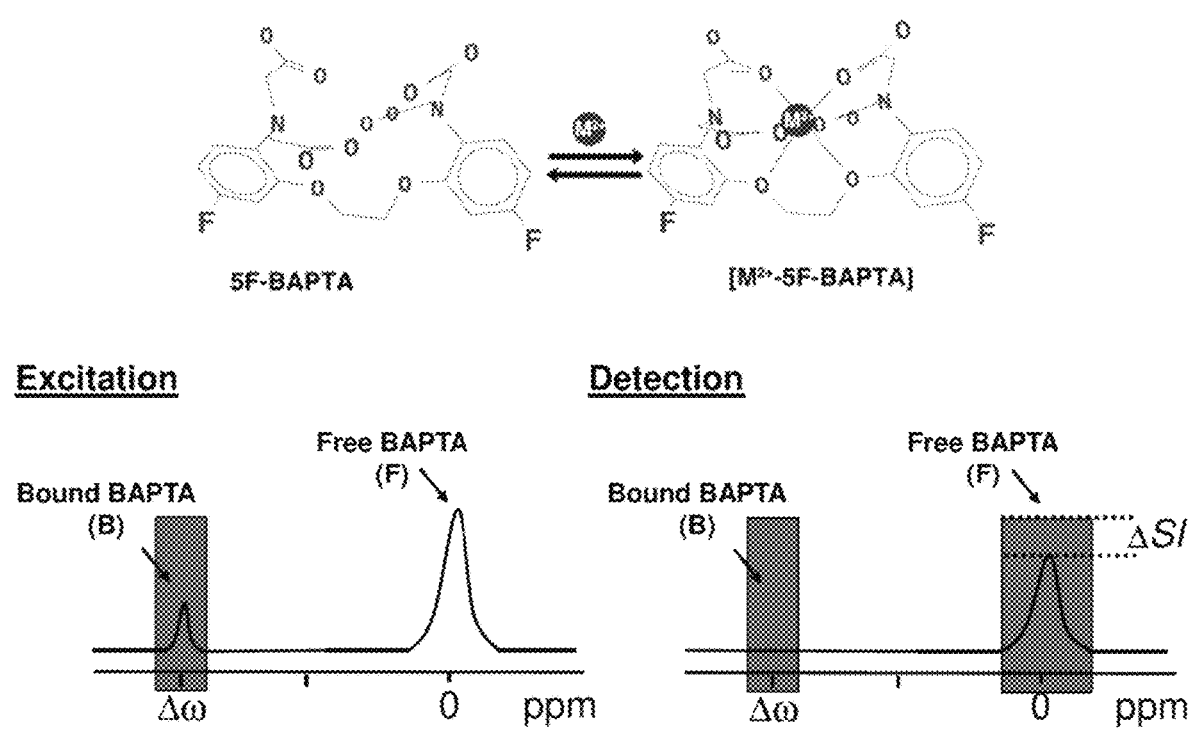

FIG. 15 demonstrates the mechanism of CEST-MRI by using exchangeable $^{19}$F-based molecule.

Figures 16A, 16B, 16C:
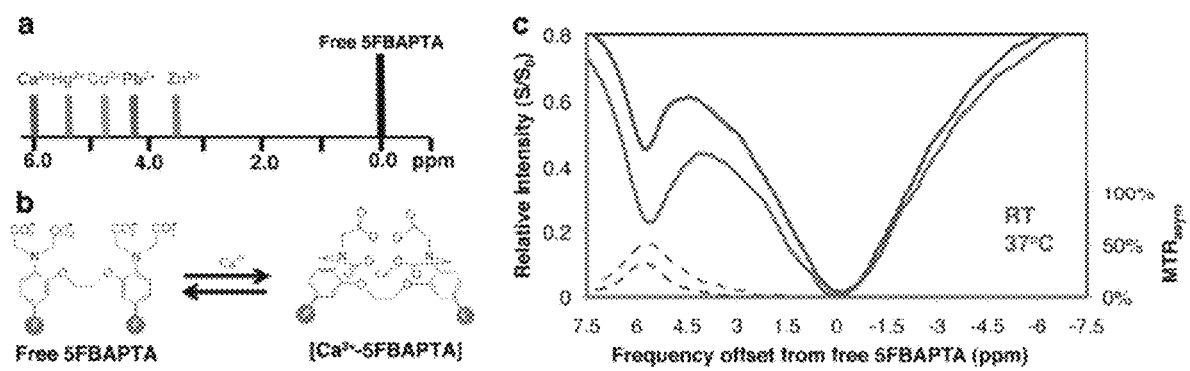

FIGS. 16a-c): a) Schematic illustration of the chemical shift offsets ( . . . ) at the 19F NMR spectrum of 5F-BAPTA upon chelation with different bivalent cations; b) demonstration of the dynamic exchange process between free and $Ca^{2+}$-bound 5F-BAPTA; c) $^{19}$F-CEST spectra (solid lines) and MTRasym plots (dashed lines) for the complex [$Ca^{2+}$-5F-BAPTA] at room temperature (RT) and 37° C. obtained at 11.7T.

Figures 17A, 17B, 17C:
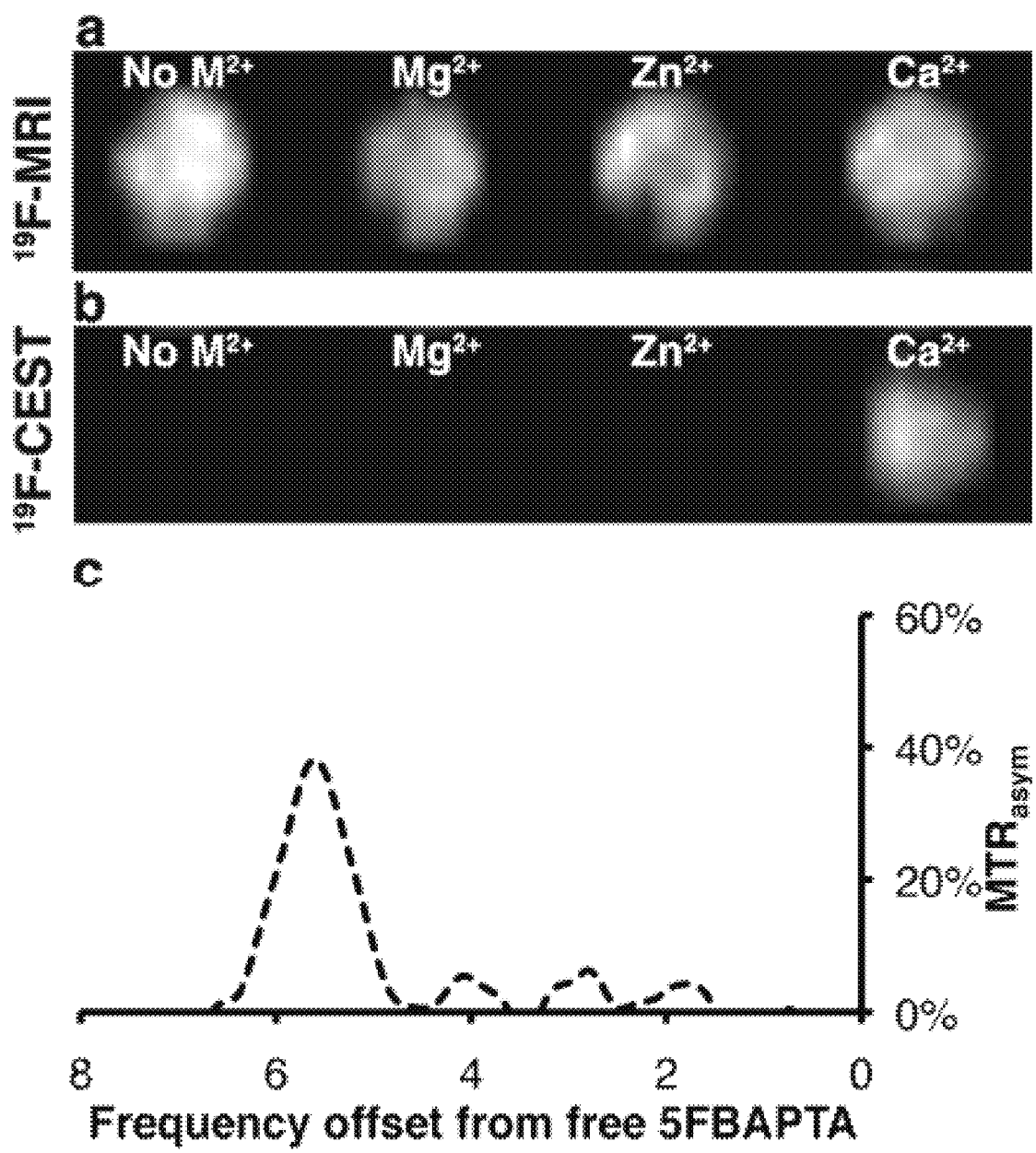

FIGS. 17a-c): a) $^{19}$F MRI of tubes containing 10 mM of 5F-BAPTA obtained at 16.4T, tubes contained either no $M^{2+}$ content or one of the ions $Mg^{2+}$, $Zn^{2+}$ or $Ca^{2+}$ at 100 µM concentration; b) MTRasym maps (Δω=5.8 ppm) obtained from the 19F-CEST experiment of the tubes shown in a; c) MTRasym plots (dashed lines) of the $Ca^{2+}$ containing tube.

Figures 18A, 18B, 18C:
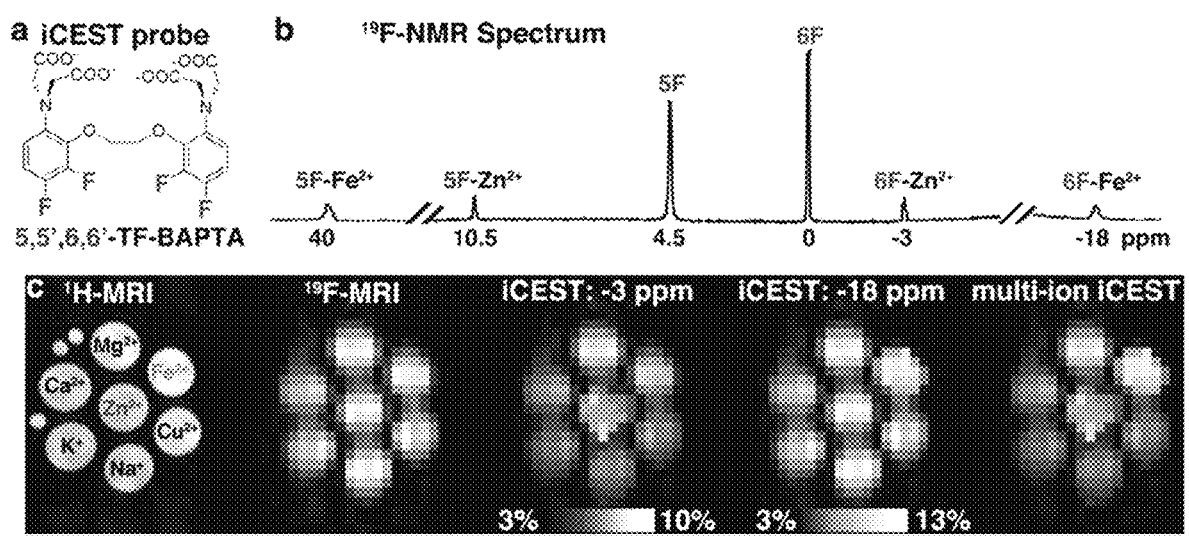

FIGS. 18a-c): a) Chemical structure of 5,5', 6,6'-tetrafluoro-BAPTA (TF-BAPTA). b) $^{19}$F NMR spectrum (470 MHz) of 5 mM TF-BAPTA in the presence of 0.5 mM $Zn^{2+}$ or $Fe^{2+}$. c) $^{1}$H MRI, $^{19}$F MRI, and iCEST Δω=−2.8 ppm or Δω=−18 ppm) overlaid on $^{19}$F MRI. The far right shows the $^{19}$F multicolor multi-ion iCEST image for 10 mM TF-BAPTA and 200 µM metal ion (i.e., $Ca^{2+}$, $Mg^{2+}$, $Zn^{2+}$, $Fe^{2+}$, $Cu^{2+}$, Na or $K^+$, as noted in FIG. 18c with B1=3.6 T/2 s.

Figures 19A, 19B, 19C:
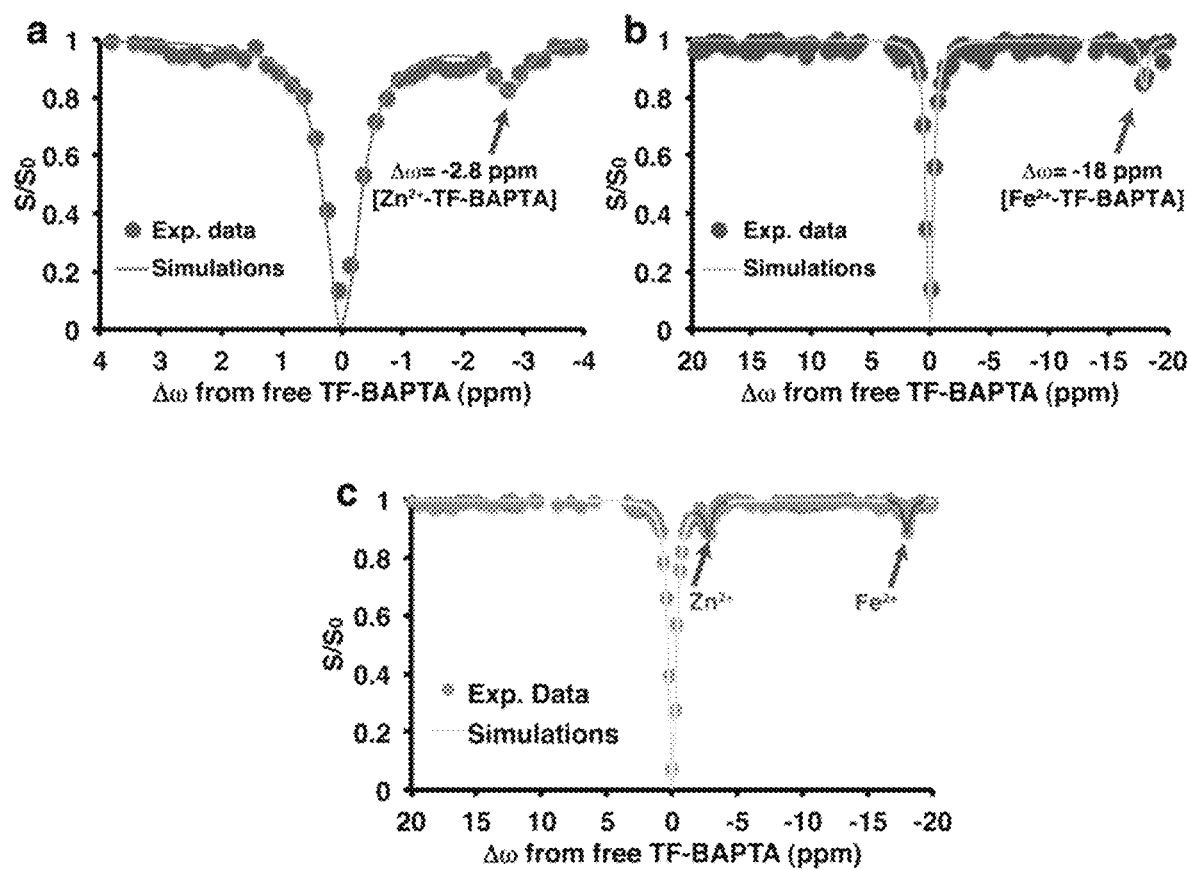

FIGS. 19a-c): a-b) Corresponding $^{19}$F-iCEST spectra for the samples shown in FIG. 18c, containing 10 mM of TF-BAPTA and 200 µM of $Zn^{2+}$ (a, red) and $Fe^{2+}$ (b, green). Circles represent the average experimental signal, solid lines represent Bloch simulations (two pool model). Arrows point to the AU of the [$M^{2+}$5F-BAPTA] complex where M preferably represents $Zn^{2+}$ or $Fe^{2+}$. c) $^{19}$F-iCEST spectra for a sample containing both $Zn^{2+}$ and $Fe^{2+}$ (not shown in FIG. 18), with Bloch simulations (solid line) performed using a three-pool model.

Figure 20:
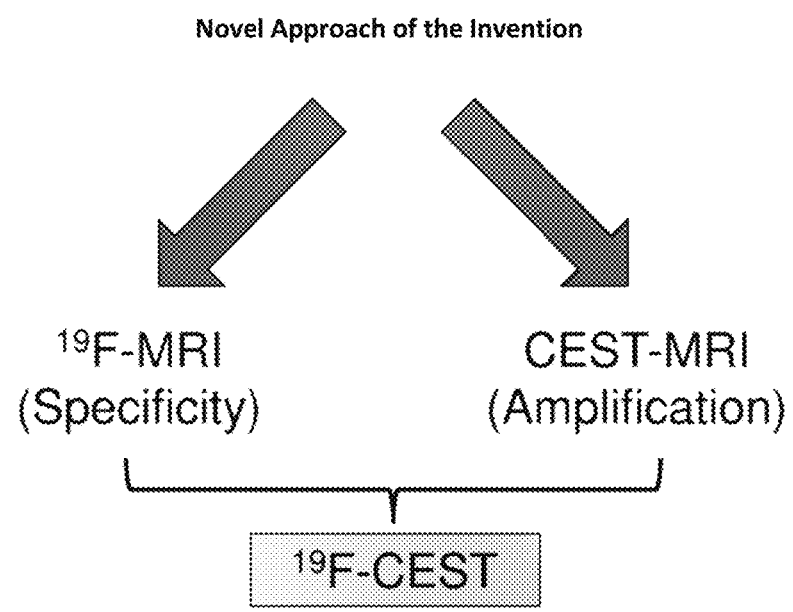

FIG. 20 shows the approach undertaken by the present inventors.

Figure 21:
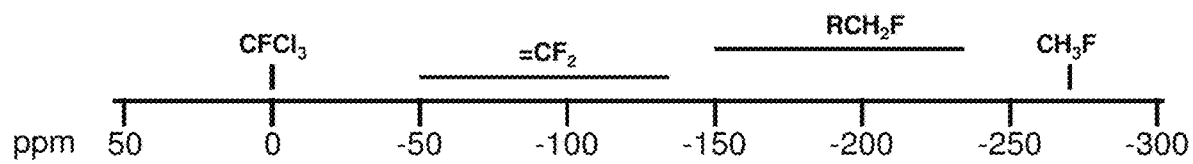

FIG. 21 shows exemplary methods of the invention using large range of $^{19}$F chemical shifts (about 20 times that of $^{1}$H) and high sensitivity of $^{19}$F chemical shifts to the details of the local environment.

DETAILED DESCRIPTION OF THE INVENTION

Fluorescent metal ion sensors have been developed for the purpose, for example, studying intracellular calcium (R. Y. Tsien, *Biochemistry* 19(1980); 2396), which enables a better understanding of calcium signals (*Cell Calcium* 40 (2006) 561). Many metal ion sensors derive from the foundational calcium sensor molecules, which were designed by tagging a fluorophore onto the backbone of a metal chelator to elicit a metal-dependent fluorescence response (L. M. Hyman et al., *Coordination Chemistry Reviews*, 256 (2012), 2333-2356).

Among those calcium sensors, many share a chelating backbone of 1,2-bis(o-aminophenoxy)ethane-N,N,N',N'-tetraacetic acid (BAPTA), with the following structure:

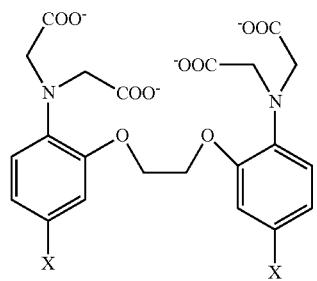

(*Biochemistry* 19(1980); 2396). Currently, imaging dynamic changes in $Ca^{2+}$ levels is restricted to fluorescence based methodologies which are limited by low tissue penetration and as a result do not allow in vivo $Ca^{2+}$ imaging in deep tissues (Mank, M. et al., *Chem Rev* 2008, 108, 1550; and Tsien, R. Y. *Annu Rev Neurosci* 1989, 12, 227). As of today, a non-invasive means of detecting free $Ca^{2+}$ in a deep tissue remains a formidable challenge.

The present inventors discovered a novel approach for sensing the presence of biologically relevant metal ions (specifically, $Ca^{2+}$), by using a strategy, in which the amplification effects of chemical exchange saturation transfer (CEST) is combined with the broad range in chemical shifts found in $^{19}$F NMR to obtain MR images of the metal ions. The inventors exploited the chemical shift change (Δω) of $^{19}$F upon binding of $Ca^{2+}$ to a difluoro derivative of [1,2,-bis(oaminophenoxy)ethane-N,N,N',N', tetra-acetic acid], e.g., 5F-BAPTA with the following structure:

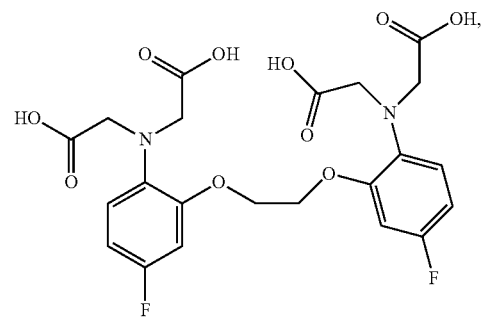 [SMILES: O=C(O)CN(CC(=O)O)c1ccc(F)cc1OCCOc1cc(F)ccc1N(CC(=O)O)CC(=O)O]

2,2',2'',2'''-(2,2'-(Ethane-1,2-diylbis(oxy))bis(4-fluoro-2, 1-phenylene))bis(azanetriyl)tetraacetic acid (alias, 1,2-bis-[2-bis(carboxymethyl)amino-5-fluorophenoxy]ethane; "5F-BAPTA").

FIG. 15 demonstrates the mechanism of CEST-MRI by using exchangeable $^{19}$F-based molecule.

Specifically, the inventors applied a CEST MRI contrast mechanism to $^{19}$F-modified M+-chelates. In a typical CEST MRI contrast mechanism, a dynamic exchange process between radiofrequency labeled protons and bulk water is exploited for contrast enhancement. In particular, the inventors employed a saturation transfer approach that couples $^{19}$F- and CEST-MRI for specifically sensing the presence of $M^{2+}$ ions through their substrate binding kinetics, an approach called ion CEST (iCEST). Using radiofrequency (RF) labeling at the bound ion-$^{19}$F frequency, (co[$M^{2+}$-chelate]), and detection of label transfer to the free chelate $^{19}$F frequency, (ω-chelate) (0 ppm), the adopted approach is able to amplify the signal of bound the metal ions by a factor of hundreds, depend on T1 and the exchange rate.

FIG. 20 illustrates the approach undertaken by the present inventors.

The $^{19}$F-MRI approach offers advantages due to the high gyromagnetic ratio of $^{19}$F (94% of that of $^{1}$H), 100% natural isotopic abundance of $^{19}$F, and the negligible amount of naturally occurring fluorine in soft biological tissues, which results in "hot spot" images without background signal. In addition, the large range of $^{19}$F chemical shifts (about 20 times than that of $^{1}$H) and the sensitivity of $^{19}$F chemical shifts to the details of the local environment is another benefit for iCEST-based applications.

Moreover, by using the iCEST approach, the contrast from low concentration solutes [M+-chelate] is amplified through back-and-forward chemical exchange and observed on the signal of the high concentration free chelate. Compared to the $^{1}$H CEST imaging, which is based on water, the $^{19}$F based approach enables detection of metal ions at lower concentrations through simply reducing the free chelate concentrations, as the contrast is dependent on the ratio of ion to agent.

Additionally, the present disclosure also provides compositions and methods that allow simultaneously detection of more than one metal ion (e.g., $K^+$, Na, $Ca^{2+}$, $Mg^{2+}$, $Cu^{2+}$, $Fe^{2+}$ and $Zn^{2+}$). For example, by adding $^{19}$F atoms to the 6 position of 5F-BAPTA to obtain TF-BAPTA (see, e.g., FIG. 18a), it became possible to detect both $Zn^{2+}$ and $Fe^{2+}$. Adding one $^{19}$F atom to the BAPTA backbone dramatically changes the binding properties of TF-BAPTA (London et al., 1994, Am J Physiol 266:1313). At the same time, the added $^{19}$F-atom induces $k_{ex}$ values that allow detection of $Zn^{2+}$ and $Fe^{2+}$ with $^{19}$F-iCEST MRI. Advantageously, the specificity of iCEST to simultaneously detect different metal ions using the same sensor provides a new ability to rationally design novel MRI probes.

Definitions

Before further description of the invention, and in order that the invention may be more readily understood, certain terms are first defined and collected here for convenience.

As used in the specification and claims, the singular form "a", "an" and "the" include plural references unless the context clearly dictates otherwise. For example, the term "a cell" includes a plurality of cells, including mixtures thereof. The term "a nucleic acid molecule" includes a plurality of nucleic acid molecules.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The term "administration" or "administering" includes routes of introducing the compound of the invention to a subject to perform their intended function. Examples of routes of administration that may be used include injection (subcutaneous, intravenous, parenterally, intraperitoneally, intrathecal), oral, inhalation, rectal and transdermal. The pharmaceutical preparations may be given by forms suitable for each administration route. For example, these preparations are administered in tablets or capsule form, by injection, inhalation, eye lotion, ointment, suppository, etc. administration by injection, infusion or inhalation; topical by lotion or ointment; and rectal by suppositories. Oral administration is preferred. The injection can be bolus or can be continuous infusion. Depending on the route of administration, the compound of the invention can be coated with or disposed in a selected material to protect it from natural conditions which may detrimentally affect its ability to perform its intended function. The compound of the invention can be administered alone, or in conjunction with either another agent as described above or with a pharmaceutically-acceptable carrier, or both. The compound of the invention can be administered prior to the administration of the other agent, simultaneously with the agent, or after the administration of the agent. Furthermore, the compound of the invention can also be administered in a pro-drug form which is converted into its active metabolite, or more active metabolite in vivo.

The phrase "in combination with" is intended to refer to all forms of administration that provide an a compound of the invention (e.g. a compound selected from any of the formulae described herein) together with a second agent, such as a second compound selected from any of the formulae described herein, or an existing therapeutic agent used for a particular disease or disorder, where the two are administered concurrently or sequentially in any order.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. Preferred alkyl groups have from 1 to 8 carbon atoms in the alkyl backbone (e.g., $C_1$-$C_8$ alkyl). As will be clear from context, the term "alkyl" as used herein further includes divalent alkylene groups (e.g., —(CH$_2$)$_n$—, wherein n is a positive integer, e.g., 1 to 8), and can further include oxygen, nitrogen, sulfur or phosphorous atoms replacing one or more carbons of the hydrocarbon backbone, e.g., oxygen, nitrogen, sulfur or phosphorous atoms. Thus, for example, in a compound of the formula:

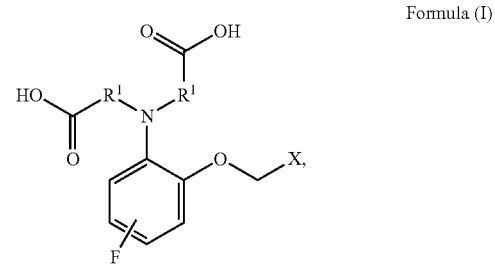

Formula (I)

if each $R^1$ is independently "$C_{1-3}$ alkyl", then each $R^1$ is independently $C_{1-3}$ alkylene. For convenience, $C_0$alkyl used herein refers to a bond or a H atom.

Moreover, the term alkyl (or alkylene) as used throughout the specification and sentences is intended to include both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)). The term "alkyl" also includes unsaturated aliphatic groups analogous in length and possible substitution to the alkyls described above, but that contain at least one double or triple bond respectively.

The term "alkoxy" refer to a O-alkyl group.

The term "aryl" as used herein, refers to the radical of aryl groups, including S- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, with said heteroatoms selected from O, N, and S, and the remainder ring atoms being carbon. Heteroaryl groups may be optionally substituted with one or more substituents. Examples of heteroaryl groups include, but are not limited to, pyridyl, furanyl, benzodioxolyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, and indolyl. In one embodiment of the invention, heteroaryl refers to thienyl, furyl, pyridyl, or indolyl.

The term "associating with" refers to a condition of proximity between a chemical entity or compound, or portions thereof, and a binding pocket or binding site on a protein. The association may be non-covalent (wherein the juxtaposition is energetically favored by hydrogen bonding or van der Waals or electrostatic interactions) or it may be covalent.

The language "biological activities" of a compound of the invention includes all activities elicited by compound of the invention in a responsive cell. It includes genomic and non-genomic activities elicited by these compounds.

"Biological composition" or "biological sample" refers to a composition containing or derived from cells or biopolymers. Cell-containing compositions include, for example, mammalian blood, red cell concentrates, platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, saliva, placental extracts, a cryoprecipitate, a cryosupernatant, a cell lysate, mammalian cell culture or culture medium, products of fermentation, ascites fluid, proteins induced in blood cells, and products produced in cell culture by normal or transformed cells (e.g., via recombinant DNA or monoclonal antibody technology). Biological compositions can be cell-free. In a preferred embodiment, a suitable biological composition or biological sample is a red blood cell suspension. In some embodiments, the blood cell suspension includes mammalian blood cells. Preferably, the blood cells are obtained from a human, a non-human primate, a dog, a cat, a horse, a cow, a goat, a sheep or a pig. In preferred embodiments, the blood cell suspension includes red blood cells and/or platelets and/or leukocytes and/or bone marrow cells.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

By "agent" is meant a polypeptide, polynucleotide, cell, or fragment, or analog thereof, small molecule, or other biologically active molecule.

The term "enantiomers" refers to two stereoisomers of a compound which are non-superimposable mirror images of one another. An equimolar mixture of two enantiomers is called a "racemic mixture" or a "racemate."

The language "improved properties" refers to any activity associated with a responsive MRI contrast agent of the invention that reduces its toxicity and/or enhances its effectiveness in sensing or detecting biologically relevant metal ions in vitro or in vivo. In one embodiment, this term refers to any qualitative or quantitative improved property of a compound of the invention, such as reduced toxicity.

The term "optionally substituted" is intended to encompass groups that are unsubstituted or are substituted by other than hydrogen at one or more available positions, typically 1, 2, 3, 4 or 5 positions, by one or more suitable groups (which may be the same or different). Such optional substituents include, for example, hydroxy, halogen, cyano, nitro, $C_1$-$C_8$alkyl, $C_2$-$C_8$ alkenyl, $C_2$-$C_8$alkynyl, $C_1$-$C_8$alkoxy, $C_2$-$C_8$alkyl ether, $C_3$-$C_8$alkanone, $C_1$-$C_8$alkylthio, amino, mono- or di-(C1-$C_8$alkyl)amino, halo$C_1$-$C_8$alkyl, halo$C_1$-$C_8$alkoxy, $C_1$-$C_8$alkanoyl, $C_2$-$C_8$alkanoyloxy, $C_1$-$C_8$alkoxycarbonyl, —COOH, —CONH$_2$, mono- or di-($C_1$-$C_8$alkyl)aminocarbonyl, —SO$_2$NH$_2$, and/or mono or di($C_1$-$C_8$alkyl)sulfonamido, as well as carbocyclic and heterocyclic groups. Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substituents).

The term "isomers" or "stereoisomers" refers to compounds which have identical chemical constitution, but differ with regard to the arrangement of the atoms or groups in space.

The term "obtaining" as in "obtaining a compound" is intended to include purchasing, synthesizing or otherwise acquiring the compound.

Responsive MRI Contrast Agents

In certain embodiments, the invention features $^{19}$F-based responsive MRI contrast agent(s) for detecting and/or sensing $Ca^{2+}$ ions. The $Ca^{2+}$ responsive MRI contrast agents include, for example, a compound of Formula (I), or a salt or ester thereof:

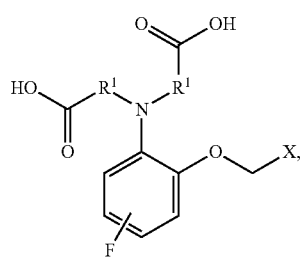

Formula (I)

Wherein
$R^1$, each independently, is $C_{1-3}$ alkyl,
X is COOH or

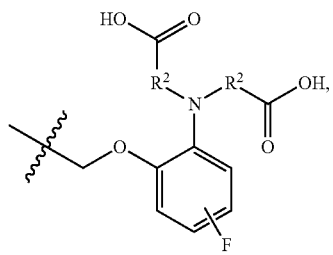

and
$R^2$, each independently, is $C_{1-3}$ alkyl.

In one embodiment, each of R's in Formula (I) is —$CH_2$—. In another embodiment, X in Formula (I) is

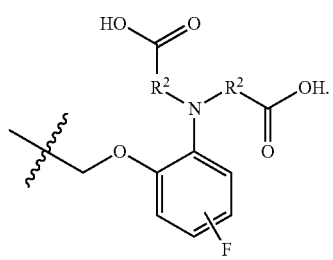

Exemplified $Ca^{2+}$ responsive MRI contrast agents include, such as,

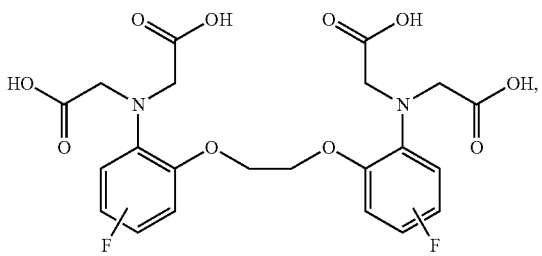

or a salt or ester thereof.

As a specific example, the $Ca^{2+}$ responsive MRI contrast agent used herein is 2,2',2'',2'''-(2,2'-(ethane-1,2-diylbis(oxy))bis(4-fluoro-2,1-phenylene))bis(azanetriyl)tetraacetic acid (alias, 1,2-bis-[2-bis(carboxymethyl)amino-5-fluorophenoxy]ethane; "5F-BAPTA"), or a salt or ester thereof.

Another example of the $Ca^{2+}$ responsive MRI contrast agent is

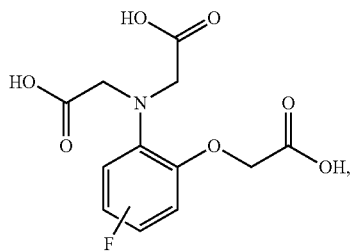

or a salt or ester thereof.

Also featured herein are $^{19}$F-based $Zn^{2+}$ responsive MRI contrast agents. In certain embodiments, the $Zn^{2+}$ responsive MRI contrast agent is a compound of Formula (II), or a salt or ester thereof:

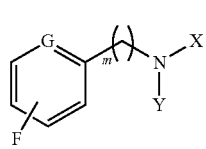

(II)

Wherein
G is C or N;
m is 1, 2, or 3;
X and Y, each independently, are selected from the group of H, —$C_{1-3}$alkyl-COOH, —$C_{1-6}$alkyl, —$C_{0-3}$alkyl-aryl, and —$C_{0-3}$alkyl-heteroaryl, wherein said aryl moiety and said heteraryl moiety are substituted by F, and are further optionally substituted by one or more alkoxy and/or $C_{1-3}$alkyl.

One embodiment of Formula (II) provides that G is N.

In a certain embodiment, at least one of X and Y in Formula (II) is a fluorine-substituted —$C_{0-3}$alkyl-heteroaryl. The heteroaryl can be, for example, pyridyl and thienyl.

In still another embodiment, at least one of X and Y is —$C_{1-3}$ alkyl-COOH.

In particular embodiments, the $Zn^{2+}$ responsive MRI contrast agents include compounds of the following formulae, or a salt or ester thereof:

(III)
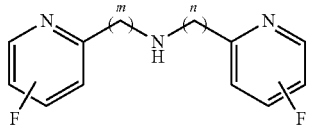

(IV)
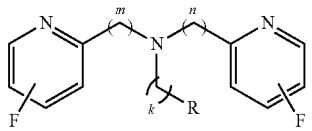

(V)
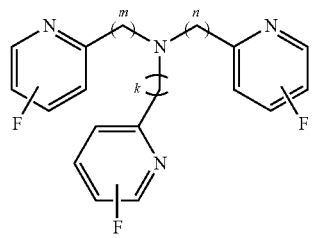

m, n, k = 1, 2, 3

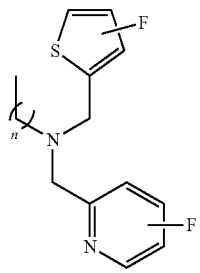

(VII)
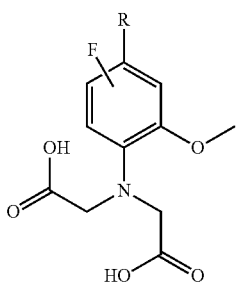

(VIII)
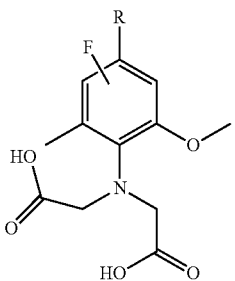

-continued (IX)
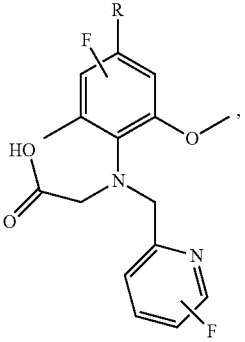

Wherein
m, n, and k, each independently, are 1, 2, or 3; and R is —$C_{1-3}$ alkyl.

The invention also features other $Zn^{2+}$ responsive MRI contrast agents, such as, a compound of Formula (X), or a salt or ester thereof:

(X)
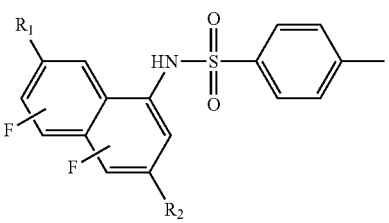

Wherein $R_1$ and $R_2$, independently, are alkoxy or $C_{1-3}$alkyl.

Also provided herein are $^{19}$F-based responsive MRI contrast agent(s) for detecting and/or sensing $Mg^{2+}$ ions. The $Mg^{2+}$ responsive MRI contrast agents of the invention include, for example, a compound of Formula (XI), or a salt or ester thereof:

(XI)
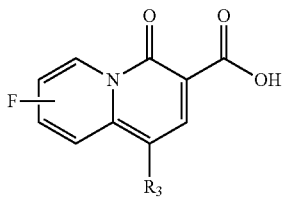

Wherein $R_3$ is H, —$C_{1-3}$ alkyl, or

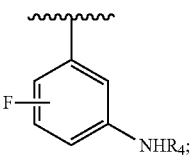

and $R_4$ is H, or —$C_{1-3}$ alkyl.

The invention also provides $^{19}$F-based responsive MRI contrast agent(s) for detecting and/or sensing $Fe^{2+}$ ions. The $Fe^{2+}$ responsive MRI contrast agents of the invention include, for example, a compound of Formula (XII) to (XIV), or a salt or ester thereof:

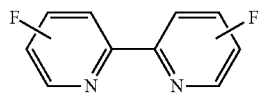 (XII)

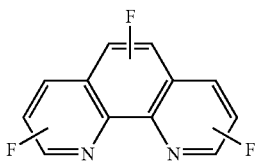 (XIII)

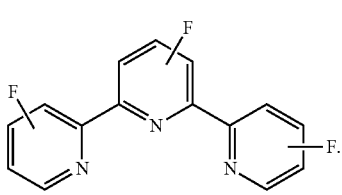 (XIV)

In certain embodiments, the invention features the use of a salt or ester of a compound of the above formulae. Suitable salts that can be used include those well known in the art (see, e.g., Berge et al. (1977) "Pharmaceutical Salts", *J. Pharm. Sci.* 66:1-19). Such a salt can be an inorganic salt (e.g., a sodium salt, a potassium salt, and a cesium salt, and etc.) and an organic salt. The esters used herein are pharmaceutically acceptable esters. In particular embodiments, the invention features acetoxymethyl (AM) esters acetate esters of the compounds of the above formulae.

It is desired that the $^{19}$F-based responsive MRI contrast agents are prepared and administered in good cell permeable forms.

As an example, 5F-BAPTA can be used and/or administered in one of the following salt/ester forms:

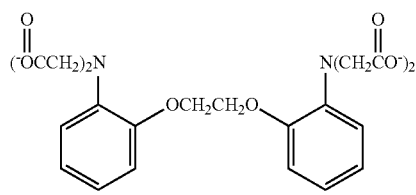

4 K$^+$

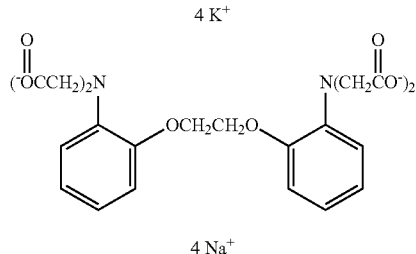

4 Na$^+$

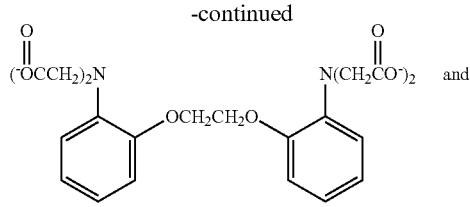

4 Cs$^+$ (CH$_3$COCH$_2$OCCH$_2$)$_2$N  N(CH$_2$COCH$_2$OCCH$_3$)$_2$, all of which are cell permeant.

The invention also provides $^{19}$F-based responsive MRI contrast agent(s) for detecting and/or sensing multiple metal ions simultaneously (e.g., K$^+$, Na$^+$, Ca$^{2+}$, Mg$^{2+}$, Cu$^{2+}$, Fe$^{2+}$ and Zn$^{2+}$). The multiple metal ion responsive MRI contrast agents of the invention include, for example, a compound of Formula (XV), or a salt or ester thereof:

Formula XV

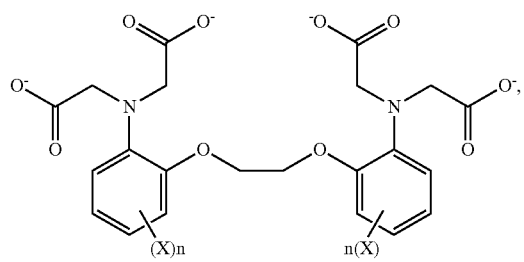

wherein X is selected from the group consisting of F and one or more of F, Cl, Br, and I, and n is 2-4. In another embodiment, X is F, and n is 1-4. In a preferred embodiment, X is F and n is 2.

Also included herein are stereoisomers (including regioisomers, diastereomers, and enantiomers), hydrates, and solvates of the compounds provided supra.

Methods and Kits

Metals are essential for sustaining all forms of life, but alterations in their cellular homeostasis are connected to severe human disorders, including cancer, diabetes and neurodegenerative diseases (*Nat Chem Biol,* 2008; 4: 168-175). For example, during transplanting human islet in a diabetes therapy, the vast majority of the islet are beta cells secreting insulin and the main ions that could be detected to determine their functionality are Calcium and zinc (FIG. 3).

Figure 3:
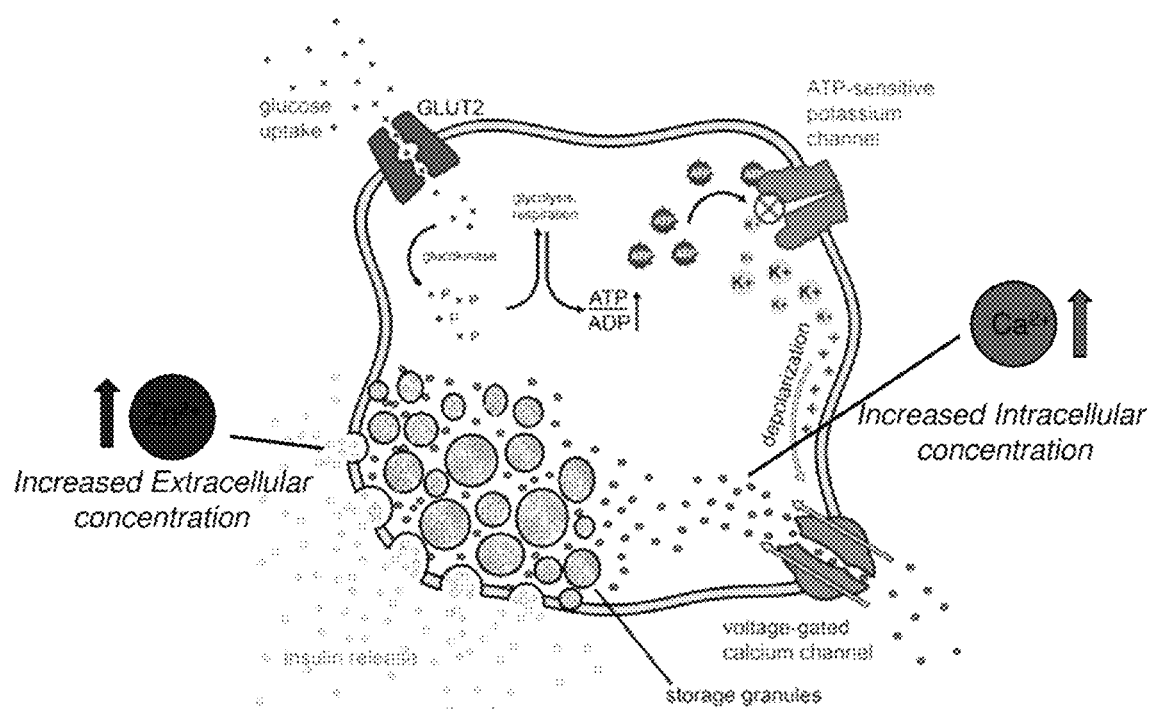
FIG. 3 is a cartoon demonstrating a process involving transplanting human islet for diabetes therapy; the vast majority of the islets are beta cells secreting insulin and the main ions to be detected to determine their functionality are calcium and zinc.

FIG. 3 demonstrates:

a) Glucose is transported into the beta cell by type 2 glucose transporters (GLUT2). Once inside, the first step in glucose metabolism is the phosphorylation of glucose to produce glucose-6-phosphate. This step is catalyzed by glucokinase—it is the rate-limiting step in glycolysis, and it effectively traps glucose inside the cell;

b) As glucose metabolism proceeds, ATP is produced in the mitochondria.

c) The increase in the ATP:ADP ratio closes ATP-gated potassium channels in the beta cell membrane. Positively charged potassium ions (K$^+$) are now prevented from leaving the beta cell.

d) The rise in positive charge inside the beta cell causes depolarization.

e) Voltage-gated calcium channels open, allowing calcium ions ($Ca^{2+}$) to flood into the cell.

f) The increase in intracellular calcium concentration triggers the secretion of insulin via exocytosis.

Many metal ion indicators are well characterized as well as commercially available, especially for optical-imaging based approaches.

The invention relates to $^{19}F$-CEST-MRI methods for detecting and/or sensing metal ions in a biological sample or tissue. Specifically, the invention provides a non-invasive means of detecting and/or sensing free metal ions in a deep tissue.

Figure 2:
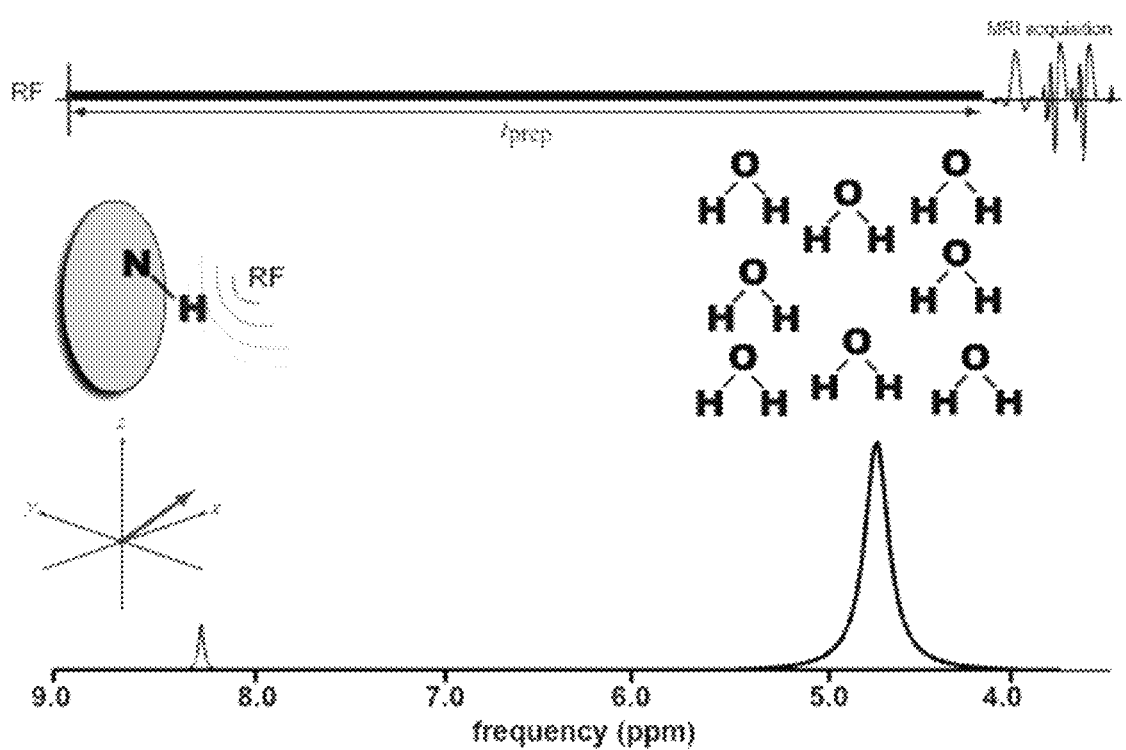
FIG. 2 demonstrates the contrast mechanism of CEST-MRI.

The CEST contrast mechanism has also been applied to generate MRI-based contrast from reporter genes. The process in FIG. 2 demonstrates how the CEST contrast is generated, which is generally through the dynamic exchange process between an exchangeable proton of the biomarker of interest and the surrounding water protons. To detect such agents, the magnetization of some of their exchangeable protons is nullified by applying a selective radiofrequency saturation pulse at the specific resonance frequency (chemical shift) of the target protons. Due to exchange of the "saturated" agent protons with surrounding water protons, the net water signal is reduced thus enhancing the MRI contrast.

The inventors have discovered that chemical saturation transfer is applicable for $^{19}F$-based MRI. For example, the inventors found that $Ca^{2+}$ could be monitored with specificity and high sensitivity with iCEST MRI using 5F-BAPTA, e.g., $Ca^{2+}$ could be detected in the presence of competitive metal ions. It is believed that the responsive agent ($^{19}F$) is the contrast generator ($^{19}F$).

In a particular embodiment, the invention presents a novel approach for specifically sensing the presence of $Ca^{2+}$ in which the amplification strategy of chemical exchange saturation transfer (CEST) is combined with the broad range in chemical shifts found in $^{19}F$ NMR to obtain MR images of $Ca^{2+}$. The chemical shift change ($\Delta\omega$) of $^{19}F$ upon binding of $Ca^{2+}$ to a difluoro derivative of [1,2,-bis(oaminophenoxy) ethane-N,N,N',N', tetra-acetic acid], also named as 5F-BAPTA, by RF labeling at the bound-19F frequency, $\omega_{[Ca-5F-BAPTA]}$, and detecting the label transfer to the free-$^{19}F$ frequency, $\omega_{5F-BAFTA}$. Through the substrate binding kinetics, the signal of $Ca^{2+}$ onto free 5F-BAPTA is amplified. Thus, the method of the invention enables an indirect detection of low $Ca^{2+}$ concentrations with high sensitivity.

In one aspect, provided herein is a method of obtaining a magnetic resonance (MR) image of a metal ion in a biological sample or tissue, said method comprising
a) introducing a $^{19}F$-based responsive magnetic resonance imaging (MRI) contrast agent to the biological sample or tissue containing the metal ion; and
b) imaging the biological sample or tissue using a chemical exchange saturation transfer (CEST)-based MRI technique.

Another aspect of the invention provides a method of detecting or sensing a metal ion in a biological sample or tissue comprising background ions. The method comprises
a) introducing to the biological sample or tissue $^{19}F$-based responsive magnetic resonance imaging (MRI) contrast agents, wherein at least one of the $^{19}F$-based responsive MRI contrast agents is bound to the metal ion to produce a chelation complex;
b) radiofrequency (RF) labeling of $^{19}F$ frequency in said chelation complex; and
c) detecting label transfer to $^{19}F$ frequency in a $^{19}F$-based responsive MRI contrast agent free of metal ion chelation.

The methods of the invention can be applied to many metal ions. In particular embodiments, the metal ion is a divalent metal ion (e.g., $Ca^{2+}$, $Zn^{2+}$, $Mg^{2+}$, $Fe^{2+}$, $Cu^{2+}$, $Ba^{2+}$, $Sr^{2+}$, $Cd^{2+}$, $Pb^{2+}$, $Co^{2+}$ and $Ni^{2+}$). One embodiment provides that the metal ion is $Ca^{2+}$, $Zn^{2+}$, $Mg^{2+}$, or $Fe^{2+}$, or a combination thereof.

The methods of the invention can also be applied to other metal ions, such as, $Fe^{3+}$, $Mn^{3+}$, $K^+$, Na, $cu^{2+}$, Cu, $Gd^{3+}$, and $Eu^{3+}$, or a combination thereof.

According to the invention, the useful $^{19}F$-based responsive magnetic resonance imaging (MRI) contrast agents include those provided supra. Alternatively, other $^{19}F$-based fluorescent metal ion sensors known in the art can also be used in the invention.

As above discussed, the invention presents a novel method of detecting or sensing $Ca^{2+}$ in a biological sample or tissue comprising background ions, said method comprising
a) introducing to said biological sample or tissue a $^{19}F$-derivative of 1,2,-bis(o-aminophenoxy)ethane-N,N,N',N', tetra-acetic acid (BAPTA), or a salt or ester thereof to obtain a chelation complex containing the metal ion and the $^{19}F$-derivative; and
b) detecting a chemical shift change of $^{19}F$ through a $^{19}F$ NMR.

In one particular embodiment, the invention relates to the use of 5F-BAPTA as a $^{19}F$-based responsive MRI contrast agent for detecting and/or sensing metal ions (especially, $Ca^{2+}$).

The invention thus offers a novel method for monitoring $Ca^{2+}$ by using MRI, specifically, the method combines the conventional amplification strategy and exchange sensitivity of CEST with the $\Delta\omega$ specificity of the $^{19}F$ frequency in free and bound substrate to obtain MR images of calcium binding kinetics.

It is discovered that BAPTA and its derivatives share high ($>10^5$) selectivity for $Ca^{2+}$ over $Mg^{2+}$ of EGTA but are very much less affected by pH changes and are faster at taking up and releasing $Ca^{2+}$ (*Biochemistry* 19(1980); 2396). $^{19}F$-NMR magnetization transfer between 5F-BAPTA and its complexes was presented in literature (such as, *NMR In Biomedicine*, 7 (1994), 330-338).

Compared to $^1H$-based approach, the methods of the invention offer advantages, such as, large range of $^{19}F$ chemical shifts (about 20 times that of $^1H$); and high sensitivity of $^{19}F$ chemical shifts to the details of the local environment (FIG. 21).

The invention also provides kits for imaging free metal ions in a biological sample or tissue. The kit of the invention includes one or more $^{19}F$-based responsive MRI contrast agents (e.g., 5F-BAPTA) of the invention, and instructions for imaging free metal ions (e.g., $Ca^{2+}$) in a biological sample or tissue.

The invention also provides a method with improved specificity and sensitivity for imaging a metal ion in a biological sample or tissue containing background ions, comprising the steps of chelating said metal ion with a $^{19}F$-based responsive magnetic resonance imaging (MRI) contrast agent to obtain a chelation metal complex, and imaging said chelation metal complex using a CEST-based MRI technique.

The iCEST approach of the invention can be further extended to designing of novel responsive agents for molecular and cellular MRI applications. Any potential novel responsive agents are assessed by an optical assay (using multi-well plates) for their potentiality for the iCEST approach.

The invention also includes a method of chemically modifying commercially available chelates for metal ion detection, comprising steps of designing and synthesizing novel chelates, and screening the novel metal ions for their usefulness in the iCEST approach.

Certain design criteria for creating metal responsive MRI contrast agents can be found in Que et al. (*Chem Soc. Rev.* 2010, 39, 51-60) and Hyman et al. (*Coordination Chemistry Reviews*, 256 (2012), 2333-2356).

Further, the $^{19}$F-based iCEST MRI approach of the invention can also be widely applied in other types of applications, for example, as a method for imaging and/or analysis reactive oxygen species and other biologically relevant compounds, or as a diagnostic method for various diseases or conditions.

EXAMPLE

General Methods:

Material:

5F-BAPTA (5,5'-difluoro BAPTA): The difluoro derivative of the tetra potassium salt of [1,2,-bis(o-aminophenoxy) ethane-N,N,N',N', tetra-acetic acid], 5F-BAPTA, was purchased from Biotium, Inc. (Hayward, Calif., USA).

Sample Preparation:

5F-BAPTA was dissolved in Hepes buffer (40 mM) to a final concentration of 10 mM and the pH was adjusted to the following values: 5.6, 6.0, 6.4, 6.8, 7.0, 7.2, and 7.6. Stock 10 mM solutions of $CaCl_2$, $MgCl_2$, and $ZnCl_2$ were prepared in 40 mM Hepes buffer. Five μL of the stock solution was added to 1 mL of 10 mM 5F-BAPTA resulting in a 200:1 ratio (10 mM: 50 μM) between the free 5F-BAPTA and the $M^{2+}$ ion following by a pH adjustment. One mL of each sample (with adjusted pH) was transferred into a 8 mm NMR tube within a 25 mm NMR tube in order to center the sample in the coil for the MRI experiments.

$^{19}$F NMR Experiments:

$^{19}$F-NMR spectra were acquired with 11.7 T NMR scanner (Bruker) with a dedicated $^{19}$F coil (470 MHz). Samples contained 5F-BAPTA (5.0 mM) $M^{2+}$ (Ca2+, Mg2+ or Zn2+, 0.5 mM), 5-Fluoro-Cytosine (5-FC, 0.5 mM) and D2O (10%) that was used for signal lock. 5FC was assigned as an internal reference with a fixed frequency of −47.0 ppm. The data show that the frequency of free 5FBAPTA is affected by pH, while that of bound 5F-BAPTA is not.

Mri Experiments:

MRI experiments were performed on a vertical 16.4 T scanner (Bruker Avance system) at 37° C. A 25 mm birdcage radiofrequency coil was used to acquire both $^1$H and $^{19}$F MR images by sweeping the coil frequency from proton (700 MHz) to fluorine (658.8 MHz) frequency.

$^1$H-MRI:

A RARE sequence was used to acquire the $^1$H-MR images with the following parameters: TR/TE=5,000/7.7 ms, RARE factor=8, 1 mm slice thickness, FOV=4×4 cm, matrix size=128×128, resolution=0.3125×0.3125 mm, and 1 average (NA=1).

Magnetization Transfer Ratio (MTR) Images, iCEST Images:

The saturation transfer effect on the free 5F-BAPTA, i.e., the MTR or iCEST, was calculated for each voxel in the image by using a Lorentzian line shape fitting as described in Jones et al. (*Magn Reson Med* 2012, 67, 1579), and Liu et al. (*Molecular imaging* 2012, 11, 47).

Relaxation Times:

The same image geometry as in the $^{19}$F-CEST experiments was used for the determination of T1 and T2 of the imaged samples. For T1 measurements, a saturation recovery experiment was performed with TR values of 61, 214, 395, 615, 899, 1296 1964, and 4961 ms. A spin-echo experiment (TR=5000 ms) with multiple echoes was performed with variable echo times (TE=5, 10 15, 20, 25, 30, 35, and 40 ms) to determine the T2 value of each sample.

Bloch Equation Simulations:

Numerical solutions to the six Bloch equations including direct saturation of free 5F-BAPTA were obtained as described previously (McMahon, M. T. et al., *Magnetic Resonance in Medicine* 2006, 55, 836). The relaxation parameters for $^{19}$F used in the Bloch equations were $R_1=1/T_1$ with bound calcium (Rib)=0.71 $s^{-1}$, $R_2$ bound calcium $(R_{2b})$=29 $s^{-1}$, whereas the $R_1$ and $R_2$ values of free 5F-BAPTA ($R_{1f}$ and $R_{2f}$) were determined experimentally through inversion-recovery and saturation-recovery experiments as a function of pH on solutions containing 20 mM 5F-BAPTA as listed in Table 1 as follows:

TABLE 1

| pH | Δω (ppm) | $T_2$ (ms) | $T_1$ (ms) |
|---|---|---|---|
| 5.6 | 2.1 | 6$^a$ | 715 |
| 6.0 | 4.0 | 10 | 715 |
| 6.4 | 5.0 | 11 | 715 |
| 6.8 | 5.6 | 25 | 715 |
| 7.0 | 5.9 | 32 | 715 |
| 7.2 | 6.2 | 38 | 715 |
| 7.6 | 6.2 | N.D | 715 |

$^a$Estimated from the Bloch equation fitting
N.D. = Not Determined $^{19}$F-iCEST Experiments:

A modified RARE sequence (TR/TE=4,000/3.4 ms, RARE factor=4, 10 mm slice thickness, FOV=4×4 cm, matrix size=32×32, resolution=1.25×1.25 mm, and NA=8) including a magnetization transfer (MT) module (B1=3.6 μT) was used to acquire CEST-weighted images from −7.2 to +7.2 ppm around the resonance of the $^{19}$F atoms at the free 5F-BAPTA, which was assigned as 0 ppm. Saturation time (tsat) was either 1500 ms to 2000 ms as indicated in the text.

$^{19}$F-iCEST of 500 nM of $Ca^{2+}$:

An aqueous solution containing 0.5 mM of 5F-BAPTA and 500 nM in Hepes buffer (40 mM, pH=7.2) was transferred into a 20 mm NMR tube, which was located within a 25 mm NMR tube in order to centralize the sample in the coil for the MRI experiment. The same parameters used for $^{19}$F-iCEST experiments were used except the followings: TR=3000 ms, RARE=8, FOV=6.0 cm (resolution=1.875× 1.875 mm), and 168 averages.

$^{19}$F-CEST Experiments with 5F-BAPTA $^{19}$F-CEST experiments were performed on solutions containing 1,2-Bis-[2-bis(carboxymethyl)amino-5-fluorophenoxy]ethane (5F-BAPTA), with and without divalent cations ($M^{2+}$).

Experiments were performed on an 11.7T NMR spectrometer (Bruker). 5F-BAPTA (AnaSpec, Inc.) was dissolved in 40 mM HEPES buffer (pH=7.0) to a concentration of 5 mM, and $CaCl_2$ was dissolved to a final $Ca^{2+}$ concentration of 50 μm.

$^{19}$F-CEST spectra (z-spectra) were acquired with a saturation transfer sequence consisting of a saturation pulse (B1=4.7 μT, 4 sec) with variable offset (from −7.5 to +7.5 ppm relative to the 5FBAPTA frequency set at 0 ppm).

Experiments were performed without (room temperature, RT) and with sample heating (37° C.). The MTRasym=100× $(S_{-\Delta\omega}-S_{+\Delta\omega})/S_0$ was computed at different offsets $\Delta\omega$, where $S_0$ is the 5F-BAPTA signal without saturation.

MRI:

Imaging experiments were performed on a 16.4T MRI scanner (Bruker). 5F-BAPTA was dissolved to 10 mM in 40 mM HEPES, pH=7.0, with or without 100 μM of $M^{2+}$ ($Mg^{2+}$, $Zn^{2+}$, or $Ca^{2+}$).

$^{19}$F-CEST images were acquired using a continuous wave presaturation pulse ($B_1$=3.6 μT, 3 sec) followed by a multi-echo MRI pulse sequence (RARE, rare factor 4, TR/TE=6000/10 ms). FOV of 4×4 cm, matrix 32×32 and slice thickness 10 mm. Mean $^{19}$F-CEST spectra were derived after $B_0$ correction for each voxel using MatLab. MTRasym plots and maps were calculated.

FIG. 16a illustrates the chemical shift offsets ($\Delta\omega$) of the 5FBAPTA at the $^{19}$F NMR frequencies upon complexation with various divalent cations ($M^{2+}$) (Smith et al., *Ptoc Natl. Acad Sci, USA* 80, 1983, 7178). FIG. 16b depicts the dynamic exchange process between the free 5FBAPTA and $Ca^{2+}$-bound 5F-BAPTA, i.e., [Ca-5FBAPTA], allowing indirect detection of low Ca2+ concentrations by using saturation transfer (FIG. 16c).

FIG. 16c shows the $^{19}$F-CEST and MTRasym plots of 5 mM 5F-BAPTA in the presence of 50 μM $Ca^{2+}$ in HEPES buffer (pH=7.0). The dynamic ion exchange process between 5F-BAPTA and [Ca-5FBAPTA], which increases with temperature, results in an observed increase in the MTRasym value at $\Delta\omega$=5.8 ppm ($\Delta\omega$ of [Ca-5F-BAPTA]) resulting in a change in the 5F-BAPTA signal.

Evaluation of the Sensitivity of iCEST Contrast Approach

Figures 7A, 7B:
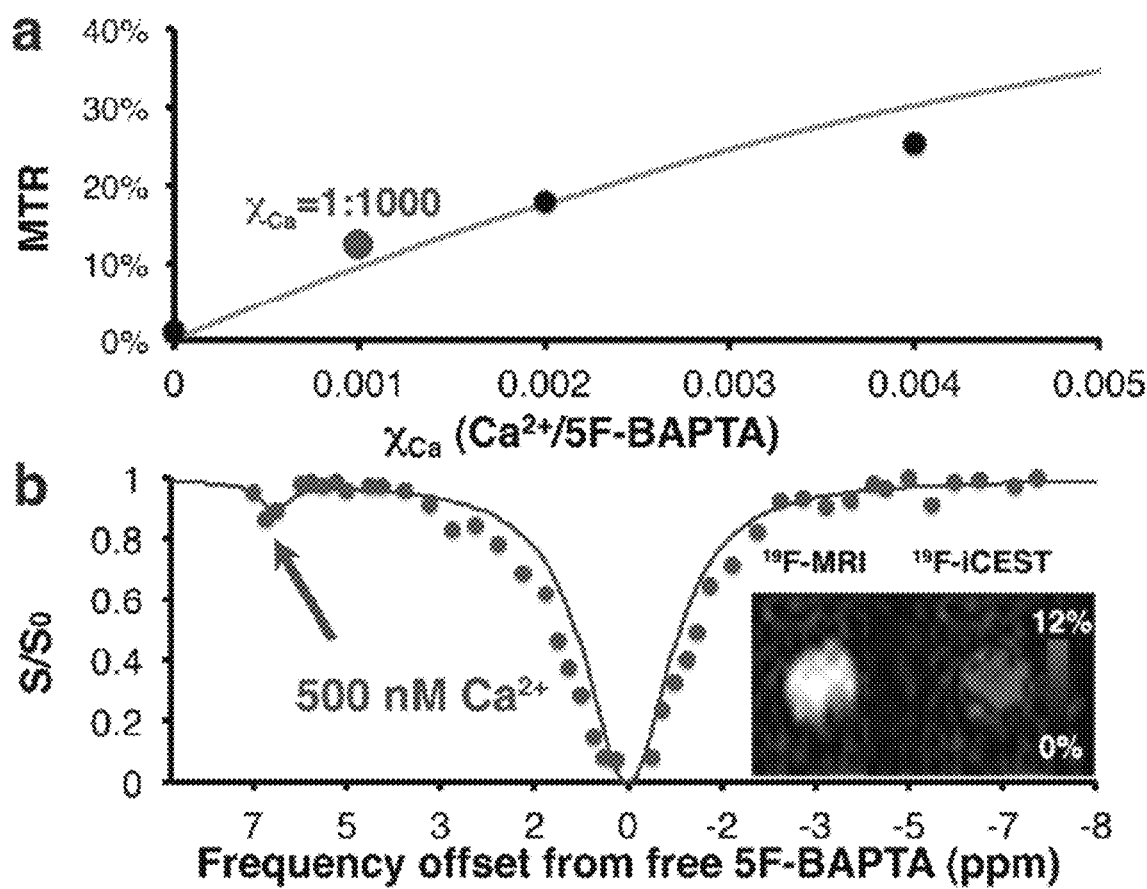
FIGS. 7a-b) show $Ca^{2+}$ sensing using iCEST: a) χCa vs. MTR plot. b) Detection of 500 nM $Ca^{2+}$ in the presence of 0.5 mM of 5F-BAPTA; inset in b) depicts $^{19}$F-MRI of the sample with an overlaid iCEST image; lines in a and b represent Bloch simulations.

The iCEST contrast of 5FBAPTA solutions (pH=7.2) at different ratios of $Ca^{2+}$ to 5F-BAPTA were examined χCa, FIGS. 7a and 12). As clearly shown in FIG. 12, $Ca^{2+}$ is easily detected with iCEST MRI at χCa=1:1000, where ~11% contrast is observed in the Zspectrum for this phantom. The same amplification using iCEST contrast was obtained when 0.5 mM 5F-BAPTA was used to detect 500 nM $C^{a2+}$ (FIG. 7b), showing the potential of iCEST to sense low $Ca^{2+}$ concentrations.

This study shows for the first time that spatial information of $Ca^{2+}$ and $Me^{+2}$ levels can be obtained using amplification of the sensitivity by iCEST with 5F-BAPTA as the ion indicator. One advantage of using 5F-BAPTA as an MRI responsive agent for detecting metal ions over $^1$H-MRI[26] or $^{129}$Xe-MRI[27] based probes is that no attachment of a contrast enhancer is required. The $^{19}$F atoms serve on the chelates as the responsive group as well as contrast generators.

The study shows the potential of exploiting the iCEST imaging concept using $^{19}$F-MRI, as 1:2000 concentration ratios are amplified to 1:20 changes in $^{19}$F signal (FIGS. 7a and 12), i.e., an amplification factor of ~100 for a kex of 190 s$^{-1}$. Moreover, the signal from low concentration solutes [$Ca^{2+}$-5F-BAPTA] is amplified through saturation transfer onto the signal of the high concentration free 5F-BAPTA. Since this contrast is dependent on χCa, lower concentrations of $Ca^{2+}$ can be detected through simply reducing the free 5F-BAPTA concentrations. This is an advantage of the iCEST approach, since this feature is not available for $^1$H CEST imaging, which is based on water.

Finally, the unique $\Delta\omega$ found for each [$M^2$-5FBAPTA] and the diversity of the obtained kex may be exploited for multi-ion MR imaging approaches in which each ion generates iCEST contrast with an identifiable amplitude and $\Delta\omega$.

$^{19}$F-CEST Properties of 5F-BAPTA in the Presence of Different Metal Ions

Figures 4A, 4B:
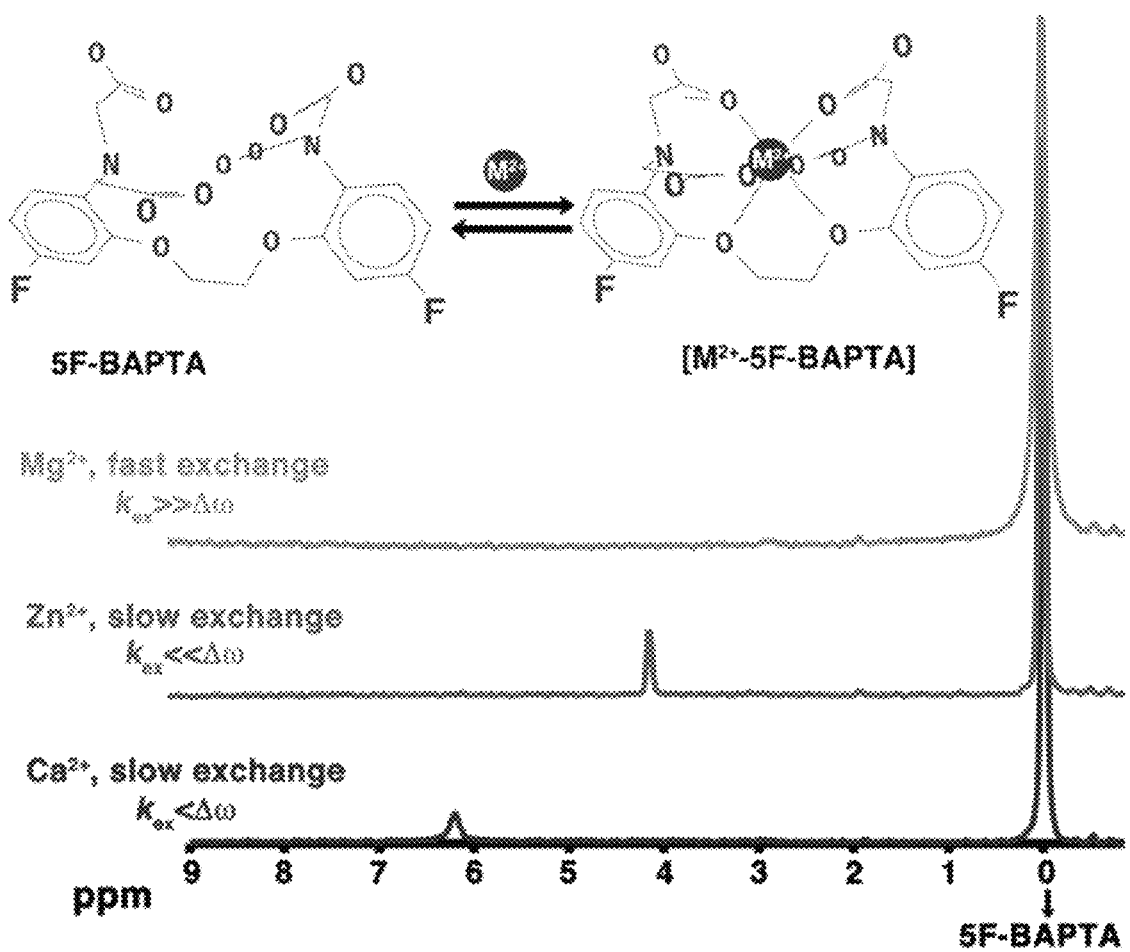
FIGS. 4a-b) show that metal ions ($M^{2+}$) binding 5F-BAPTA: a) schematic depiction of a dynamic exchange process between free 5F-BAPTA and bound $[M^{2+}$-5F-BAPTA]; b) $^{19}$F NMR spectra (470 MHz) of 5F-BAPTA in the presence of $Mg^{2+}$, $Zn^{2+}$, and $Ca^{2+}$.

FIG. 4a illustrates the dynamic exchange process between free 5F-BAPTA and its complex with $M^{2+}$, [$M^{2+}$-5F-BAPTA]. Upon $M^{2+}$ binding, there is a $^{19}$F chemical shift change (Acs) for 5F-BAPTA. If the exchange rate (kex) between $M^{2+}$-bound and free 5F-BAPTA is fast on the NMR time scale ($\Delta\omega \ll k_{ex}$), no peak can be resolved. When the $k_{ex}$ is sufficiently slow at the field strength used, a well-defined peak is observed for the [$M^{2+}$-5F-BAPTA] resonance as is shown for $Zn^{2+} \gg$ kex) and $Ca^{2+}$ ($\Delta\omega$>kex).

The observed $\Delta\omega$'s are typical and unique for each ion that is complexed by 5F-BAPTA and ranges from a few ppm in the cases of $Ca^{2+}$, $Zn^{2+}$, $Ba^{2+}$, $Cd^{2+}$, $Pb^{2+}$ and others to tens of ppm upon binding of $Fe^{2+}$, $Co^{2+}$ and $Ni^{2+}$ (Smith et al., *Proc Natl Acad Sci USA* 1983, 80, 7178; Kirschenlohr, H. L. et al., *Biochem J* 2000, 346 Pt 2, 385). The dissociation constant ($K_d$) of [$M^{2+}$-5F-BAPTA] is different for each $M^{2+}$, and as a result so is the $k_{ex}$ for the process in FIG. 4a. The $Zn^{2+}$-5F-BAPTA resonance (FIG. 4b, 4.1 ppm) is sharper than the $Ca^{2+}$-5F-BAPTA resonance (FIG. 4b, 6.2 ppm), which is correlated with their reported differences in $K_d$.

Figures 5A, 5B, 5C, 5D, 5E, 5F:
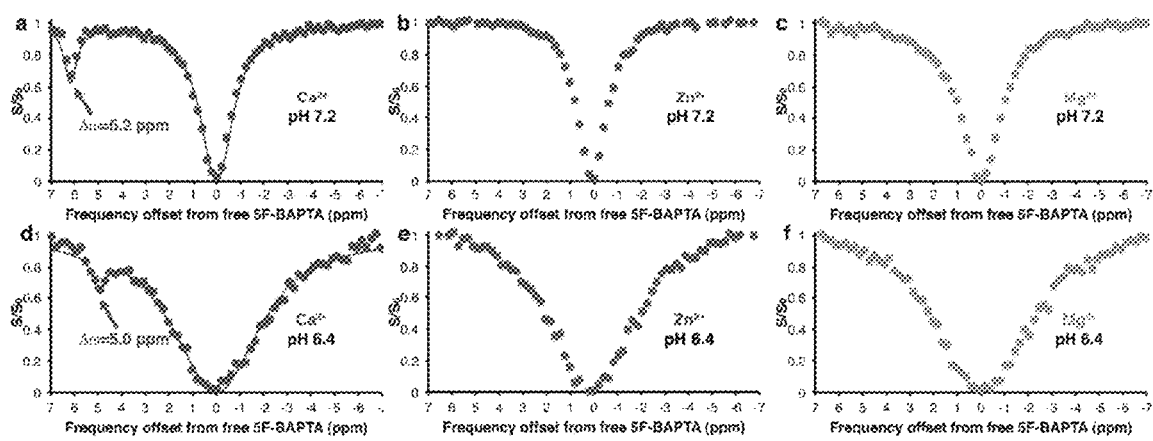
FIGS. 5a-f) are $^{19}$F-iCEST Z-spectra of solutions containing 10 mM of 5F-BAPTA and 50 µM of $M^{2+}$ ($Ca^{2+}$; $Zn^{2+}$; and $Mg^{2+}$) in 40 mM Hepes buffer with the pH of the solutions adjusted to 7.2 (a-c) or 6.4 (d-f); dots represent the raw experimental data; for $Ca^{2+}$, lines represent Bloch simulations (two pool model) and arrows point to the frequency of the [$Ca^{2+}$-5F-BAPTA] complex.

The $^{19}$F-CEST properties of 5F-BAPTA in the presence of $Ca^{2+}$ (slow-to-intermediate $k_{ex}$), $Zn^{2+}$ (very slow $k_{ex}$) and $Mg^{2+}$ (fast kex) were determined on a 16.4 T. MRI scanner and are summarized in FIG. 5 for two different pH values, i.e. 7.2 (FIG. 5a-c) and 6.4 (FIGS. 5d-f). At these concentrations, a pronounced saturation transfer contrast was detected in the $Ca^{2+}$ containing solutions (FIGS. 5a,d) but not in the $Zn^{2+}$ or $Mg^{2+}$ containing solutions (FIG. 5b,e or FIG. 5c,f, respectively).

Figures 10A, 10B, 10C, 10D, 10E, 10F:
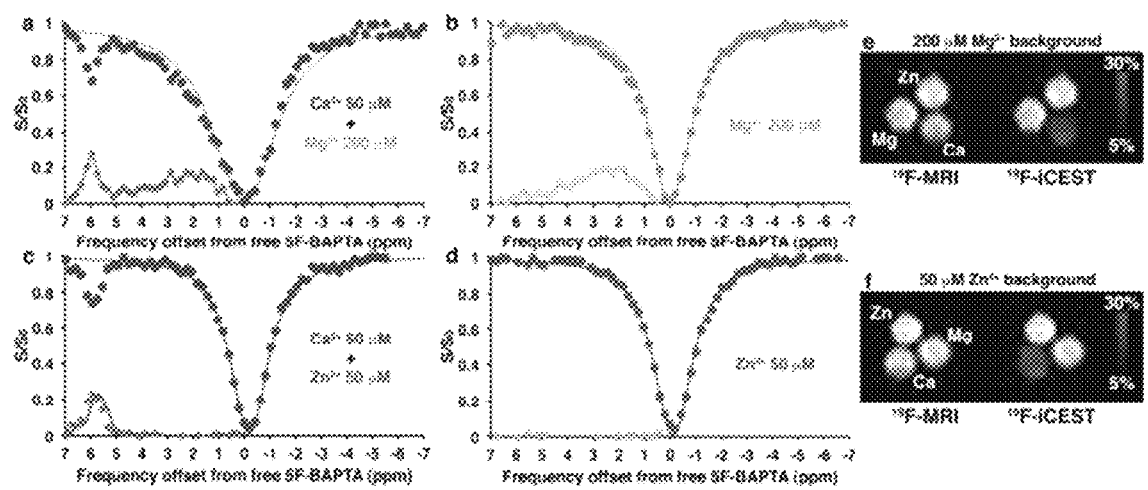
FIG. 10a-f): a-d) are $^{19}$F-iCEST Z-spectra of solutions containing a) $Ca^{2+}$ (50 µM) and $Mg^{2+}$ (200 µM); b) $Mg^{2+}$ (200 µM); c) $Ca^{2+}$ (50 µM); and d) $Zn^{2+}$ (50 µM) at pH=7.2, 37° C., and 16.4 T; e-f) are MTR asymmetry ($MTR_{asym}$) plots of the background solutions are shown for 200 µM $Mg^{2+}$ (a & b) and for 50 µM $Zn^{2+}$ (c & d); solid lines represent Bloch simulations.

Importantly, a broad asymmetry is observed at very high fractional $Mg^{2+}$ concentrations (FIG. 10b, χ(5FBAPTA/Mg)= 50:1), which peaks at 1.8 ppm, a frequency much lower than Ca2+ (FIG. 10a).

Interestingly, the $\Delta\omega$ between [Ca-5F-BAPTA] and free 5F-BAPTA was found to be dependent on pH (FIGS. 5, 6, 8, 9 and 11 and Table 1), but the $k_{ex}$ between [Ca-5F-BAPTA] and 5F-BAPTA was preserved for all examined pH values as determined by Bloch simulations (190±10 s$^{-1}$, FIGS. 5 and 8) (McMahon, M. T. et al., *Magn Reson Med* 2006, 55, 836) These results are in a good agreement with a previous report showing that the binding of $Ca^{2+}$ was unaffected at pH 6-8 using $^{19}$F-MRS.

Figure 6:
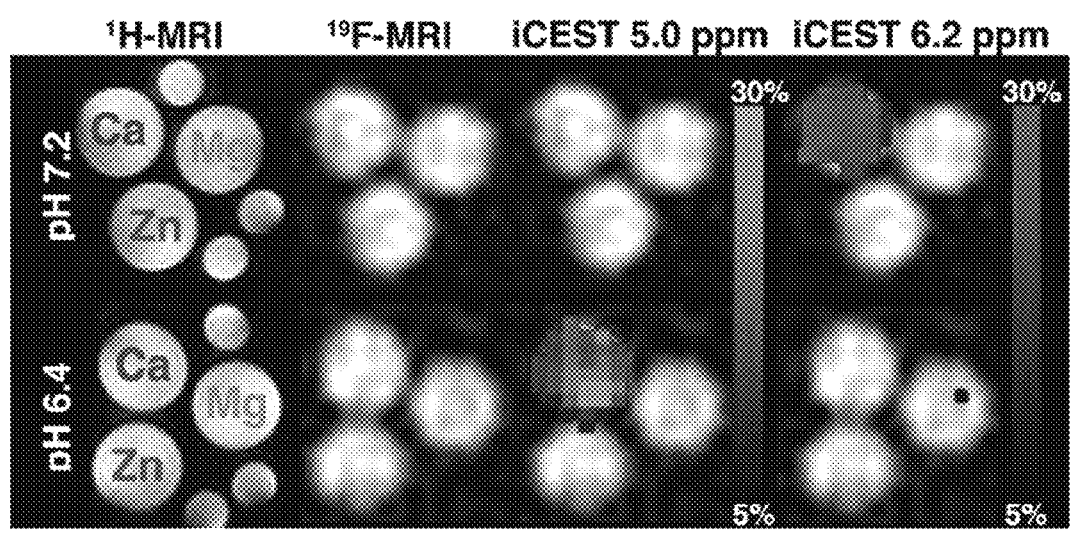
FIG. 6 shows MR images of $Ca^{2+}$ with iCEST: $^{1}$H-MRI, $^{19}$F-MRI, and iCEST (Δω=6.2 or 5.0 ppm) of $M^{2+}$ solutions with pH values of 7.2 or 6.4; each tube contains 10 mM of 5F-BAPTA and 50 µM of $M^{2+}$.
Figures 8A, 8B, 8C, 8D:
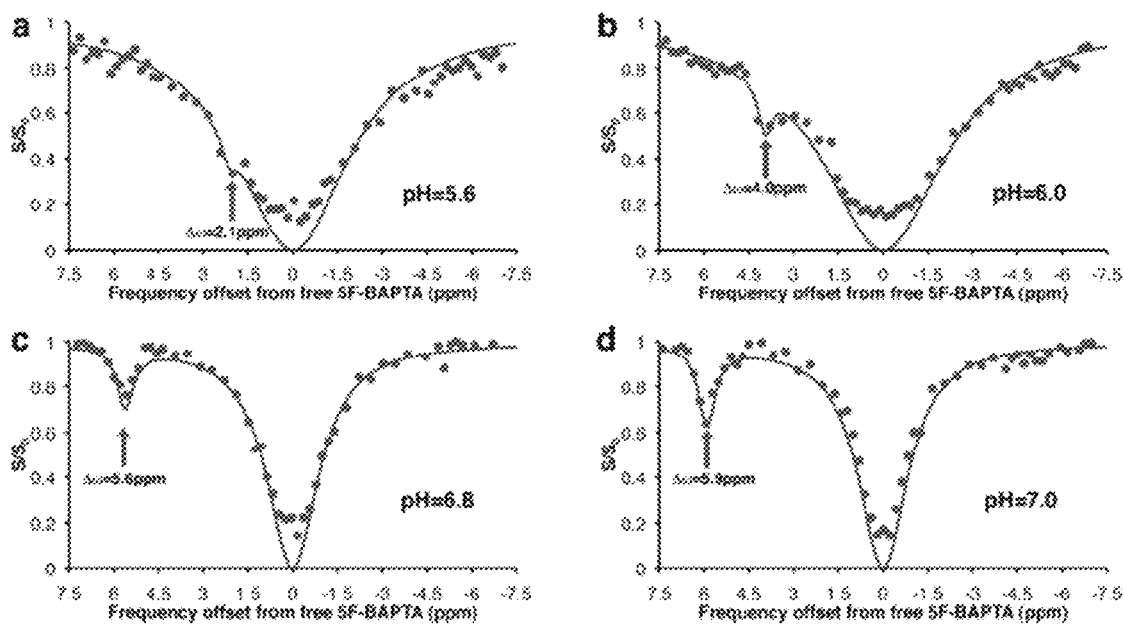
FIGS. 8a-d) are $^{19}$F-CEST spectra that show pH dependency of 5F-BAPTA: CEST-spectra of solutions containing 10 mM of 5F-BAPTA and 50 µM of $Ca^{2+}$ in 40 mM Hepes buffer at solutions with the pH adjusted to a) 5.6; b) 6.0; c) 6.8; and d) 7.0; solid lines represent Bloch simulations (two pool model) and arrows point to the Δω of the [$Ca^{2+}$-5F-BAPTA] complex.
Figure 9:
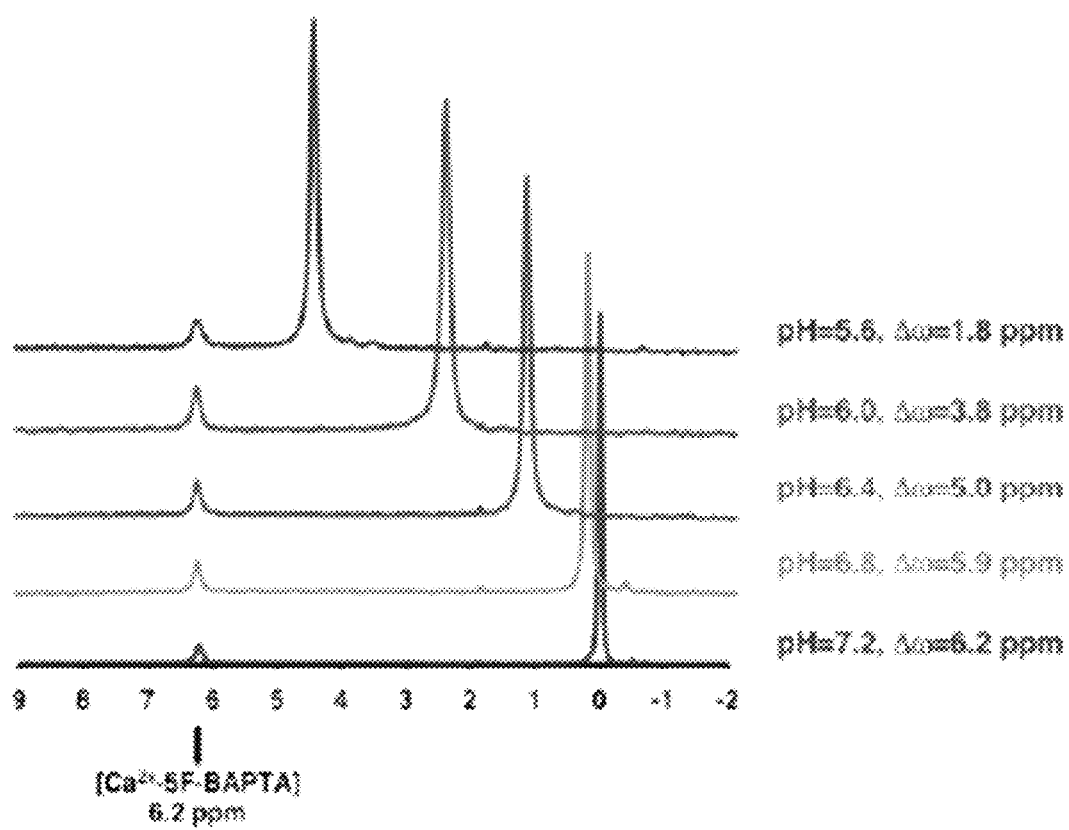
FIG. 9 presents $^{19}$F-NMR spectra showing pH dependency of 5F-BAPTA: the spectra are for solutions containing $Ca^{2+}$ (0.5 mM), 5F-BAPTA (5 mM), and 5-Fluoro-Cytosine (5FC, 0.5 mM) as internal reference (set to −47 ppm) with 10% $D_2O$; the spectra were acquired at 470 MHz, with the peak of 5-FC calibrated at −47 ppm.

$^{19}$F-NMR spectra collected with an internal reference revealed that upon pH change, the frequency of the free 5F-BAPTA shifts but not the frequency of bound $M^{2+}$-5F-BAPTA (FIG. 9). The T2 values of 5F-BAPTA are also sensitive to pH as can be seen by the broadening in the Z-spectra (FIGS. 5 and 8; and Table 1). The T2-value changes seem to be dependent on 5F-BAPTA protonation and not exchange rate dependent based on the observation that the same Z-spectra line widths were found for solutions containing $Mg^{2+}$ ($\Delta\omega \ll$kex) and $Zn^{2+}$ ($\Delta\omega \gg$kex). FIG. 6 shows MR images of the samples that have been used in this study, i.e., 10 mM of 5F-BAPTA and 50 μM of $M^{2+}$.

Figure 11:
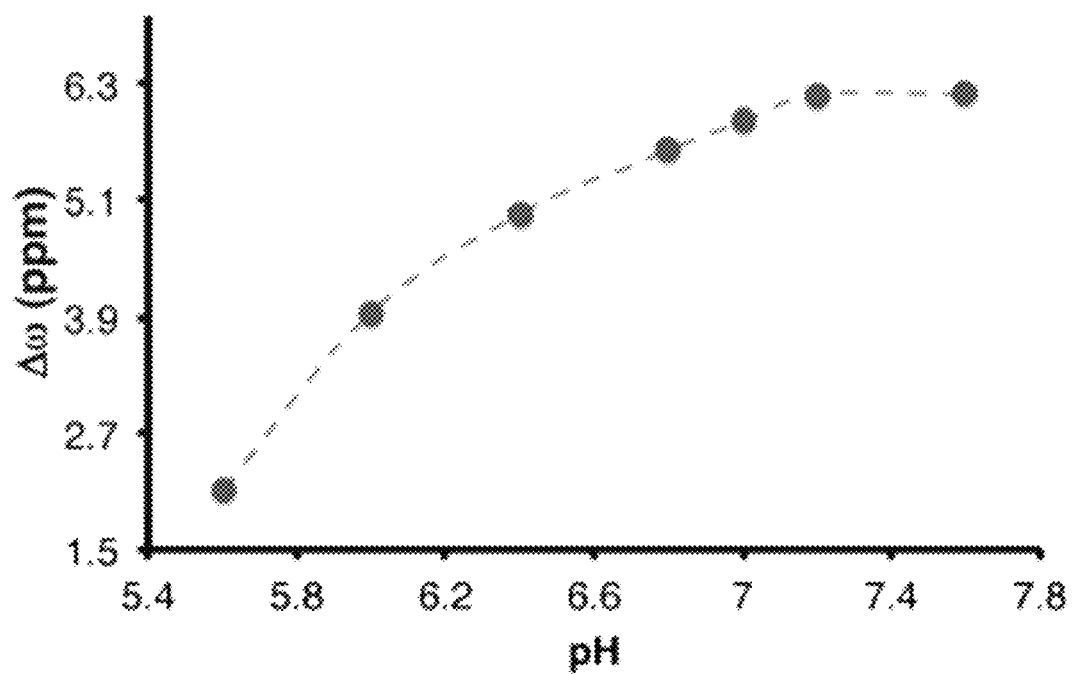
FIG. 11 presents a graph showing pH dependency of iCEST. The dependency of Δω between $Ca^{2+}$-bound and free 5F-BAPTA as obtained from iCEST Z-spectra: the phantom includes 8 mm NMR tubes containing 10 mM of 5F-BAPTA and 50 µM of $M^{2+}$ in 40 mM Hepes buffer (pH=5.6-7.6); $^{19}$F-iCEST data were acquired with $B_1$=3.6
Figures 12A, 12B, 12C, 12D, 12E, 12F, 12G:
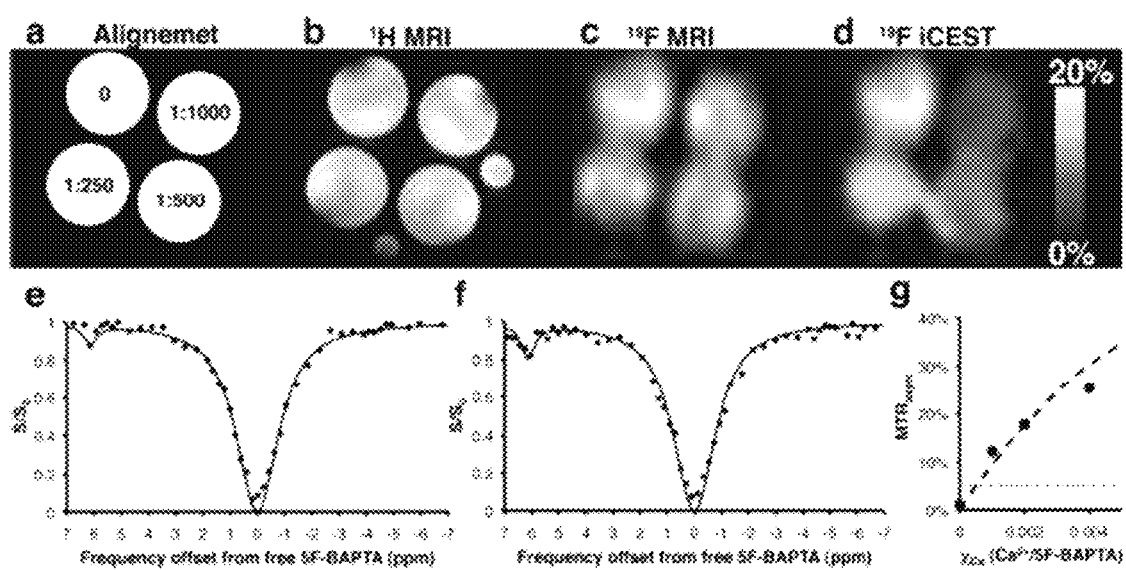

As expected no difference in MR contrast was observed between the samples when using conventional $^1$H-MRI or $^{19}$F-MRI. However, contrary to the $Mg^{2+}$- or $Zn^{2+}$-containing samples, which did not generate iCEST contrast at this concentration, a large iCEST contrast was detected for the $Ca^{2+}$ containing sample when a saturation pulse ($B_1$=3.6 μT/2000 ms) was applied at the appropriate frequency offset of the [$Ca^{2+}$-5F-BAPTA] complex, i.e., $\Delta\omega$=6.2 ppm (pH=7.2) and $\Delta\omega$=5.0 ppm (pH=6.4). FIG. 11 shows the dependence of $\Delta\omega$ on pH, with $\Delta\omega$ ranging from 2.1 ppm to 6.2 ppm for pH values of 5.6 to 7.2.

In addition, iCEST images were acquired for solutions containing mixtures of $Ca^{2+}$ and $Mg^{2+}$ (50 µM $Ca^{2+}$, 200 µM $Mg^{2+}$) and $Ca^{2+}$ and $Zn^{2+}$ (50 µM $Ca^{2+}$, 50 µM $Zn^{2+}$) with 10 mM BAPTA at pH 7.2. The iCEST contrast produced by the $Ca^{2+}$ was still significant (~22%) at $\Delta\omega$=6 ppm for all mixtures (FIG. 10). Although high $Mg^{2+}$ generates iCEST contrast at $\Delta\omega$=1.8 ppm (FIG. 10 10a-b) the larger $\Delta\omega$, smaller $k_{ex}$ of [Ca-5F-BAPTA] and its much higher iCEST contrast makes this approach better for $Ca^{2+}$ sensing (FIG. 10b, amplification factor=×10 for $Mg^{2+}$, ×100 for $Ca^{2+}$).

$Ca^{2+}$ Specificity of 5F-BAPTA

The iCest approach regarding $Ca^{2+}$ specificity was studied by using 5F-BAPTA as a metal ion indicator. The results were presented in FIGS. 13 and 14. As shown in FIGS. 13a-c, 5F-BAPTA demonstrates a high $Ca^{2+}$ specificity in a $Zn^{2+}$ background. FIGS. 14a-c, 5F-BAPTA also demonstrates a high $Ca^{2+}$ specificity in a $Mg^{2+}$ background.

The $^{19}$F-CEST MR images shown in FIG. 17 clearly demonstrate the specificity of the iCEST approach. On conventional $^{19}$F-MRI (FIG. 17a), no difference in contrast could be observed for the different tubes (no $M^{2+}$, $Mg^{2+}$, $Zn^{2+}$, and $Ca^{2+}$), as this detects only the free 5F-BAPTA. On $^{19}$F-CEST MRI, only the $Ca^{2+}$ containing solution generated contrast (FIG. 17b). Here, the saturation pulse was applied at $\Delta\omega$=5.8 ppm from the 5FBAPTA resonance (0 ppm). FIG. 17c shows the mean $^{19}$F-CEST MTRasym plot for the tube containing 5FBAPTA in the presence of $Ca^{2+}$.

The variance in the $\Delta\omega$ of [$M^{2+}$-5F-BAPTA] complex for each examined $M^{2+}$ makes $^{19}$F-CEST MRI more specific than relaxation based $^1$H MRI methodologies. The specificity is comparable to that of PARACEST agents used for $Ca^{+2}$ and $Zn^{+2}$ binding (G. Angelovski et al., Bioorg Med Chem 19, 1097 (2011); R. Trokowski et al., Angew Chem Int Ed Engl 44, 6920 (2005)), but no paramagnetic agent is needed. The higher saturation transfer effect for 5F-BAPTA obtained at 37° C. as compared to RT (FIG. 16c) is due to the faster ion exchange rate between 5F-BAPTA and [Ca-5F-BAPTA]. This confirms that the observed effect is due to the dynamic binding kinetics process.

It is contemplated that the specificity of the $^{19}$F-CEST method proposed here is not just due to the different $\Delta\omega$ values of the examined ions (FIG. 16a), but also due to the different dissociation constants ($K_d$) between 5FBAPTA and the divalent metal complex [$M^{2+}$-5F-BAPTA], which determines the exchange rate ($k_{ex}$) and therefore the $^{19}$F-CEST contrast. The $K_d$ for $Ca^{2+}$ results in slow to intermediate $k_{ex}$ on the NMR time scale (H. Gilboa et al., NMR Biomed 7, 330 (1994)), while the $K_d$ values for $Mg^{2+}$ and $Zn^{2+}$ result in $k_{ex}$ values that are too fast and too slow, respectively, preventing the observation of signal changes in the $^{19}$F-CEST experiment.

Simultaneous Detection of Multiple Metal Ions Using a Single 19F-iCEST Probe

In another embodiment of the invention, the $^{19}$F iCEST MRI approach may be extended by chemical modification of a BAPTA derivative, 5,5', 6,6'-tetrafluoro-BAPTA (TF-BAPTA, AG Scientific, Inc.), that alters the binding kinetics of metal ions and their chelates, enabling specific and simultaneous detection of $Zn^{2+}$ and $Fe^{2+}$. TF-BAPTA has the following structure:

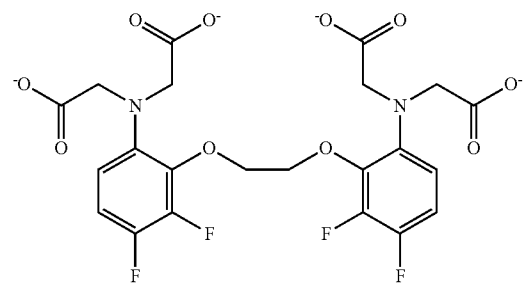

Without being bound by theory, it is believed that the above-shown acetate form allows the TF-BAPTA compound to enter into desired target cells, where the acetate may be hydrolyzed and the free acid form is released. The free acid form may allow binding of the ions to be detected. Accordingly, one of skill in the art will appreciate that the acetate form may typically be used to facilitate the transport of TF-BAPTA into the cell for in vivo imaging application, whereas ex vivo imaging applications will typically involve an appropriate free acid form of the molecule.

Methods

Figure 1:
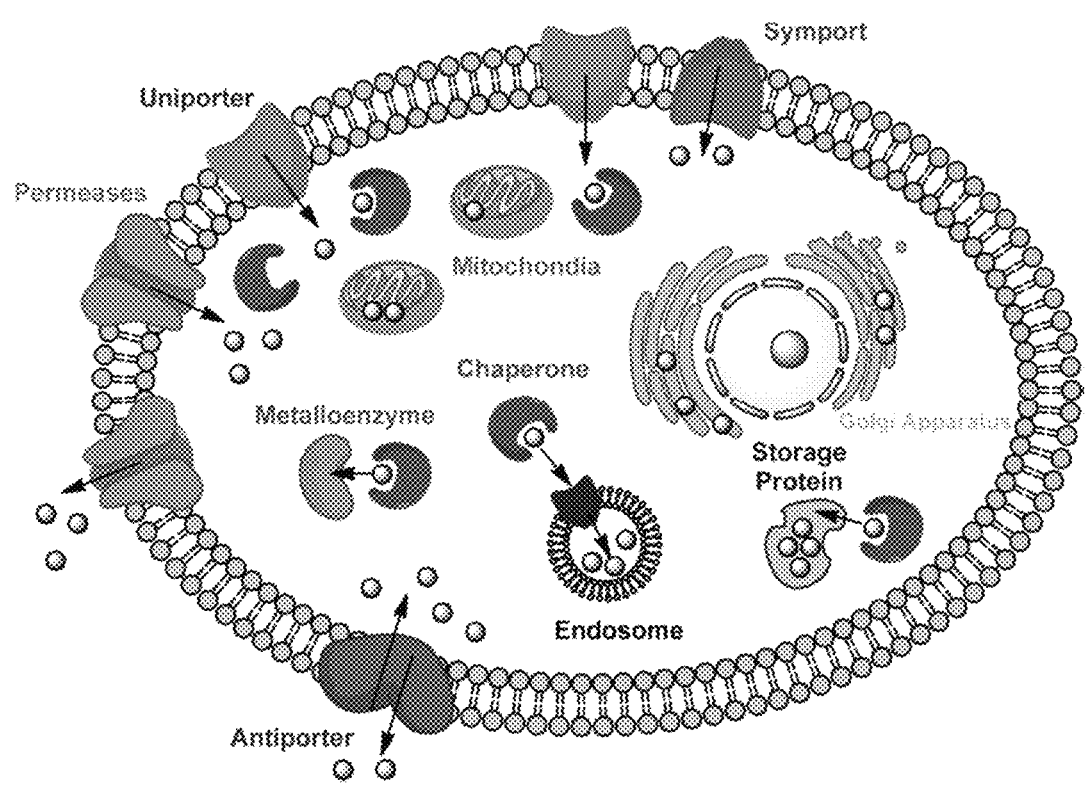
FIG. 1 is a cartoon illustrating metal ion signaling and homeostasis in many cellular processes.

Experiments were performed on solutions containing TF-BAPTA and multiple biologically relevant metal ions ($K^+$, $Na^+$, $Ca^{2+}$, $Mg^{2+}$, $Cu^{2+}$, $Fe^{2+}$ and $Zn^{2+}$) at 37° C. and pH=7.4. MR Spectroscopy as follows: TF-BAPTA was dissolved to a final concentration of 5 mM, and ions were add at 500 µM. Using 5-Fluorocytosine (5-FC) as an internal $^{19}$F reference, $^{19}$F-NMR spectra were acquired (11.7 T NMR spectrometer, Bruker). MRI: Experiments were performed on a 17.6 T MRI scanner (Bruker). TF-BAPTA was dissolved to 10 mM with 200" AM of ion. A RARE (factor 8) sequence was used to acquire 1H MRI (TR/TE=5,000/7.7 ms, 1 mm slice, FOV=2×2 cm, matrix size=128×128). For $^{19}$F MRI, the center frequency (O1) was set at the frequency of the 19F atom at the 6 position (0.0 ppm) of TF-BAPTA (FIG. 1a), while signal from the $^{19}$F located at the 5 position of TF-BAPTA (FIG. 1a-b, 4.5 ppm downfield) was suppressed. A modified RARE sequence (TR/TE=4,000/3.4 ms, RARE factor=16, 6 mm slice, FOV=2×2 cm, matrix size=32×32, and a saturation pulse B1=1.2, 2.4 or 3.6 ItT/2 s) were used to acquire $^{19}$F iCEST. Mean $^{19}$F Z-spectra (iCEST spectra), were obtained after $B_0$ correction. CEST contrasts, i.e., the magnetization transfer ratio (MTR) images were calculated after Lorentzian line shape fitting.

FIG. 18a illustrates the chemical structure of TF-BAPTA. FIG. 18b shows the $^{19}$F NMR spectra of TF-BAPTA in the presence of $Zn^{2+}$ or $Fe^{2+}$, along with the peak assignments. As shown previously for $Ca^{2+}$ binding to TF-BAPTA (London et al., 1994, Am J Physiol 266:1313), the downfield NMR peaks (10.5 ppm for $Zn^{2+}$-TF-BAPTA and 39.5 ppm for $Fe^{2+}$-TF-BAPTA) are the observed Oros of the $^{19}$F atom at the 5 position (purple, FIG. 18a), while the upfield $\Delta\omega$s are related to the $^{19}$F atom at the 6 position (green, FIG. 18a). Note that all other examined ions did not reveal additional peaks in the $^{19}$F NMR spectrum of TF-BAPTA, except for $Ca^{2+}$ which exchanges extremely fast (~30,000 s−1) with TF-BAPTA for $\Delta\omega$=9.7 ppm, shifting the peak at the 5 position upon its addition (London et al., 1994, Am J Physiol 266:1313). FIG. 18c shows the $^1$H-MRI and $^{19}$F-MRI of 7 tubes containing 10 mM TF-BAPTA and 200 µM of added ion, without any changes in $^1$H or $^{19}$F MR contrast. However, $^{19}$F iCEST showed a clear differential MR contrast between the $Zn^{2+}$ and $Fe^{2+}$ containing samples. The iCEST:−2.8 ppm and iCEST:−18 ppm images represent the $^{19}$F iCEST contrast obtained when the saturation pulse (B1=3.6 µT/2 s) was applied at Δω=−2.8 ppm and Δω=−18 ppm, respectively. These Δω values were correlated with the Δωs in the $^{19}$F NMR spectra upon addition of $Zn^{2+}$ or $Fe^{2+}$, respectively (see FIG. 18b). FIG. 19a-b shows the corresponding $^{19}$F-iCEST-spectra from the samples containing either $Zn^{2+}$ (FIG. 19a) or $Fe^{2+}$ (FIG. 19b). The dynamic ion exchange between TF-BAPTA and [$M^{2+}$-TF-FBAPTA] results in an observed iCEST effect for both ions at Δω=−2.8 ppm for [$Zn^{2+}$-TF-BAPTA] and at Δω=−18 ppm for [$Fe^{2+}$-TF-BAPTA]. Using Bloch simulations (solid lines in FIG. 19a-b, using a two pool model) the exchange rate ($k_{ex}$) between free and bound TF-BAPTA is estimated to be ~20 s−1 for both ions. Interestingly, when both ions were combined with TF-BAPTA (FIG. 19c), two distinctive peaks were obtained in the iCEST spectra, which was supported by the Bloch simulations (using a three-pool model). These data confirm that $Zn^{2+}$ and $Fe^{2+}$ can be monitored simultaneously using a single iCEST probe.

The high sensitivity of the $^{19}$F NMR spectrum Δω) values for changes in chemical environment together with the specificity of these Δωs for certain metal ions allows the development of novel responsive contrast agents for $^{19}$F-iCEST. By adding $^{19}$F atoms to the 6 position of 5F-BAPTA, which previously allowed only detection of $Ca^{2+}$ using iCEST (Bar-Shir et al., 2013, J Am Chem Soc 135:12164; Gilboa et al., 1994, NMR Biomed 7:330), to obtain TF-BAPTA (FIG. 18a), it became possible to detect both $Zn^{2+}$ and $Fe^{2+}$. Adding one $^{19}$F atom to the BAPTA backbone dramatically changes the binding properties of TF-BAPTA (London et al., 1994, Am J Physiol 266:1313). At the same time, the added $^{19}$F-atom induces $k_e$. values that allow detection of $Zn^{2+}$ and $Fe^{2+}$ with $^{19}$F-iCEST MRI. Although other $^{1}$H MRI probes for the detection of $Zn^{2+}$ can be used (Lubag et al., 2011, PNAS), the specificity of iCEST to simultaneously detect different ions using the same sensor represents a new concept for the rational design of novel MRI probes. While the observed $k_{ex}$ between bound and free TF-BAPTA is only 20 s−1 for both ions, and higher CEST effect could be obtained for higher $k_{ex}$, (van Zijl et al., 2011, Magn Reson Med 65:927) it was still possible to detect a 200 µM concentration with a 10 mM signal strength. Without being bound by theory, it is believed that this may be due to the nature of iCEST that allows the reduction of the concentration of the $^{19}$F-iCEST probe to a detectable molar ratio, a feature that is not available for $^{1}$H-CEST, which is based on water. However, further chemical modifications of the fluorinated probe may result in higher $k^{ex}$ and therefore in higher iCEST contrast.

Although a preferred embodiment of the invention has been described using specific terms, such description is for illustrative purposes only, and it is to be understood that changes and variations may be made without departing from the spirit or scope of the following claims.

INCORPORATION BY REFERENCE

All patents, published patent applications and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

We claim:

1. A method of obtaining a magnetic resonance (MR) image of a metal ion in a biological sample or tissue, comprising
    a) introducing a $^{19}$F-based responsive magnetic resonance imaging (MRI) contrast agent to said biological sample or tissue; and
    b) imaging said biological sample or tissue using a chemical exchange saturation transfer (CEST)-based MRI technique,
    wherein said $^{19}$F-based responsive MRI contrast agent is a compound of Formula (I), or a salt or ester thereof:

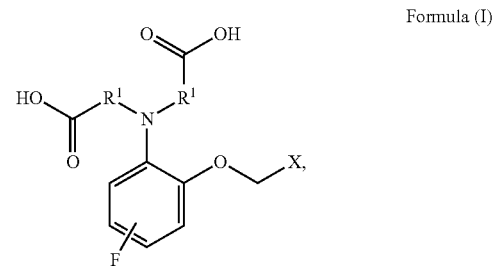

Formula (I)

wherein $R^1$, each independently, is $C_{1-3}$ alkyl, and

X is —COOH or

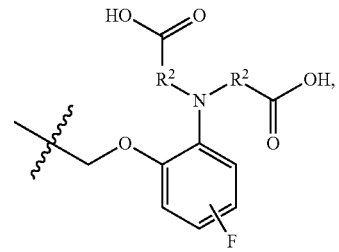

and $R^2$, each independently, is $C_{1-3}$ alkyl.

2. The method of claim 1, wherein said metal ion is a divalent metal ion.

3. The method of claim 1, wherein said metal ion is selected from the group of $Ca^{2+}$, $Zn^{2+}$, $Mg^{2+}$, $Fe^{3+}$, $Fe^{2+}$, $Mn^{3+}$, $K^+$, $Na^+$, $Cu^{2+}$, $Gd^{3+}$, and $Eu^{3+}$, or a combination thereof.

4. The method of claim 3, wherein said metal ion is $Ca^{2+}$.

5. The method of claim 3, wherein said metal ion is $Zn^{2+}$.

6. The method of claim 3, wherein said metal ion is $Mg^{2+}$.

7. The method of claim 3, wherein said metal ion is $Fe^{2+}$.

8. The method of claim 1, wherein each of $R^1$ is —$CH_2$—, and X is

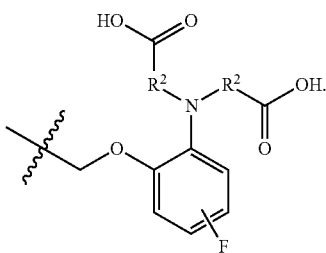

9. The method of claim 1, wherein said $^{19}$F-based responsive MRI contrast agent is selected from the group consisting of

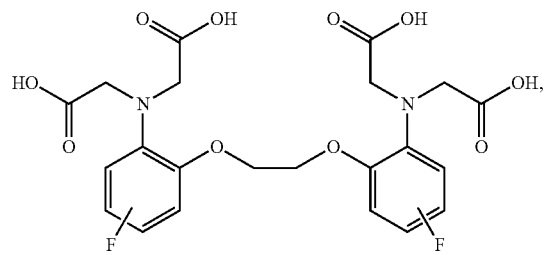

or a salt or ester thereof and

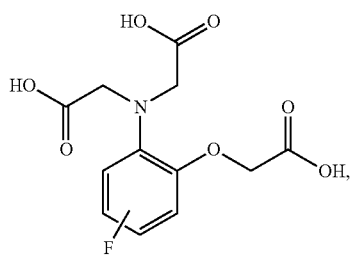

or a salt or ester thereof.

10. The method of claim 9, wherein said $^{19}$F-based responsive MRI contrast agent is 2,2',2'',2'''-(2,2'-(ethane-1,2-diylbis(oxy))bis(4-fluoro-2,1-phenylene))bis(azanetriyl) tetraacetic acid (5F-BAPTA) or a salt thereof.

11. A method
  of detecting or sensing a metal ion in a biological sample or tissue comprising background ions, comprising
  a) introducing to said biological sample or tissue a $^{19}$F-based responsive magnetic resonance imaging (MRI) contrast agent, wherein the $^{19}$F-based responsive MRI contrast agent is bound to the metal ion to produce a chelation complex;
  b) radiofrequency (RF) labeling of $^{19}$F frequency in said chelation complex; and
  c) detecting transfer of the RF labeling to $^{19}$F frequency in a $^{19}$F-based responsive MRI contrast agent free of metal ion chelation to image said biological sample or tissue by MRI,
  wherein the $^{19}$F-based responsive MRI contrast agent is a compound of Formula (I), or a salt or ester thereof:

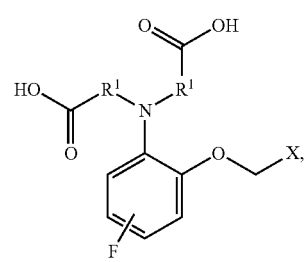

wherein
  R$^1$, each independently, is C$_{1-3}$ alkyl, and
  X is COOH or

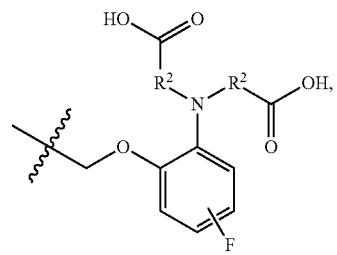

and
  R$^2$, each independently, is C$_{1-3}$ alkyl.

12. The method of claim 11, comprising detecting a chemical shift change of $^{19}$F through a $^{19}$F NMR.

13. The method of claim 11, wherein said $^{19}$F-based responsive MRI contrast agent is 5F-BAPTA.

14. The method of claim 11, wherein the metal ion is selected from the group consisting of K$^+$, Na$^+$, Ca$^{2+}$, Mg$^{2+}$, Cu$^{2+}$, Fe$^{2+}$ and Zn$^{2+}$.

15. A method of detecting or sensing a metal ion in a biological sample or tissue, comprising
  a) introducing to said biological sample or tissue a $^{19}$F-based responsive magnetic resonance imaging (MRI) contrast agent, wherein the $^{19}$F-based responsive MRI contrast agent is bound to the metal ion to produce a chelation complex;
  b) radiofrequency (RF) labeling of $^{19}$F frequency in said chelation complex; and
  c) detecting transfer of the RF labeling to $^{19}$F frequency in a $^{19}$F-based responsive MRI contrast agent free of metal ion chelation to image said biological sample or tissue by MRI,
  wherein the $^{19}$F-based responsive MRI contrast agent is a compound of Formula (XV), or a salt or ester thereof:

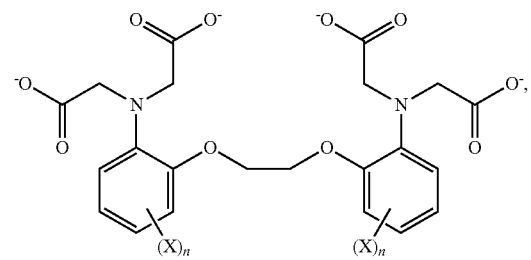

wherein X is selected from F, Cl, Br, and I, with proviso that at least one X is F, and n is 2-4.

16. The method of claim 15, wherein X is F and n is 2.

17. The method of claim 15, wherein the $^{19}$F-based responsive magnetic resonance imaging (MRI) contrast agent is 5,5',6,6'-tetrafluoro-1,2,-bis(o-aminophenoxy)ethane-N,N,N',N'-tetraacetate.

* * * * *